(12) United States Patent
Jin et al.

(10) Patent No.: US 8,168,800 B2
(45) Date of Patent: May 1, 2012

(54) Aβ-BINDING SMALL MOLECULES

(75) Inventors: Lee-Way Jin, Davis, CA (US); Kit S. Lam, Davis, CA (US); Ruiwu Liu, Sacramento, CA (US); Hyun-Seok Hong, Davis, CA (US); Izumi Maezawa, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/740,329

(22) PCT Filed: Oct. 31, 2008

(86) PCT No.: PCT/US2008/082096
§ 371 (c)(1),
(2), (4) Date: Nov. 24, 2010

(87) PCT Pub. No.: WO2009/059214
PCT Pub. Date: May 7, 2009

(65) Prior Publication Data
US 2011/0071301 A1 Mar. 24, 2011

Related U.S. Application Data

(60) Provisional application No. 60/985,138, filed on Nov. 2, 2007.

(51) Int. Cl.
*C07D 491/052* (2006.01)

(52) U.S. Cl. .................................. 548/302.1
(58) Field of Classification Search ............... 548/302.1
See application file for complete search history.

(56) References Cited

U.S. PATENT DOCUMENTS

2005/0019255 A1   1/2005   Zachek et al.
2005/0070538 A1   3/2005   Cheng et al.

FOREIGN PATENT DOCUMENTS

WO   WO 2006/050501   5/2006

OTHER PUBLICATIONS

Song et al., Tetrahedron, (2004), 60(39), pp. 8605-8612.*
International Search Report Dated Jan. 28, 2009, for related International Patent Application No. PCT/US2008/082096, filed Oct. 31, 2008.

* cited by examiner

*Primary Examiner* — Laura L. Stockton
(74) *Attorney, Agent, or Firm* — Kilpatrick Townsend & Stockton LLP

(57) ABSTRACT

In one aspect, the present invention provides for compounds and labeled compounds of Formula I, and pharmaceutical compositions thereof. In another aspect, the present invention provides for methods of using compounds or labeled compounds of Formula I for various therapeutic and imaging purposes, including, but not limited to, treating Alzheimer's disease in patient and imaging Aβ peptide aggregates in a patient.

10 Claims, 13 Drawing Sheets

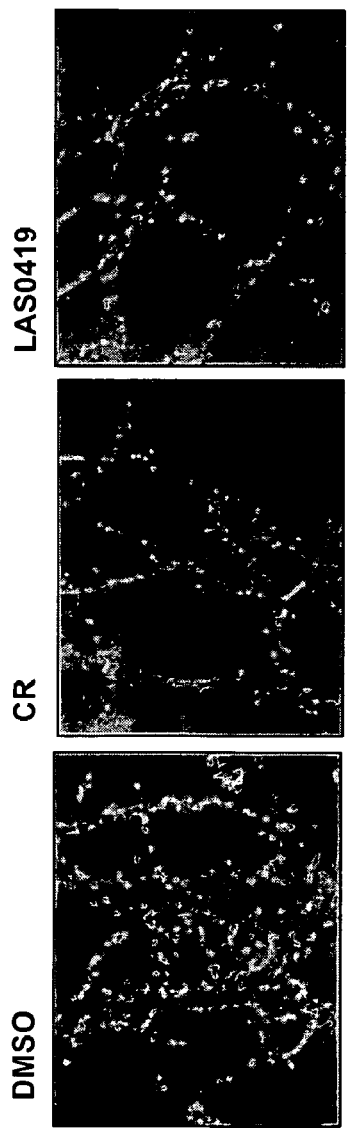
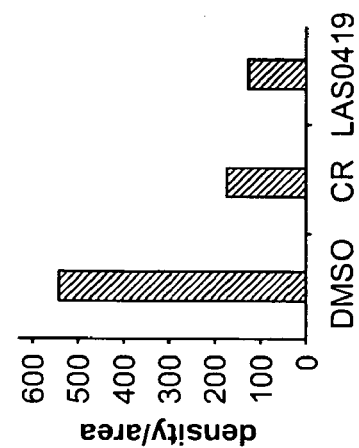
FIG. 6

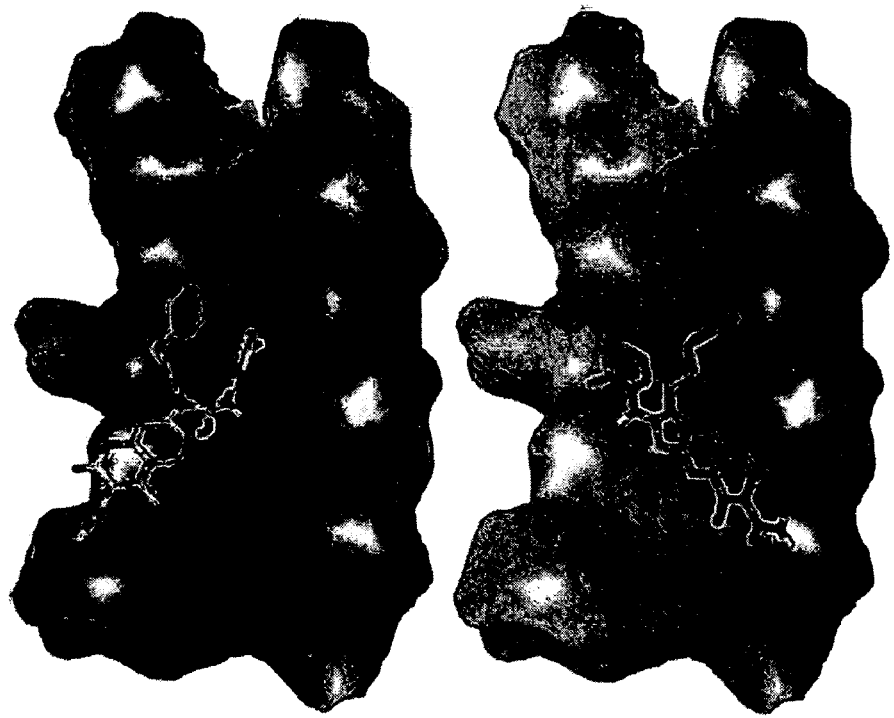
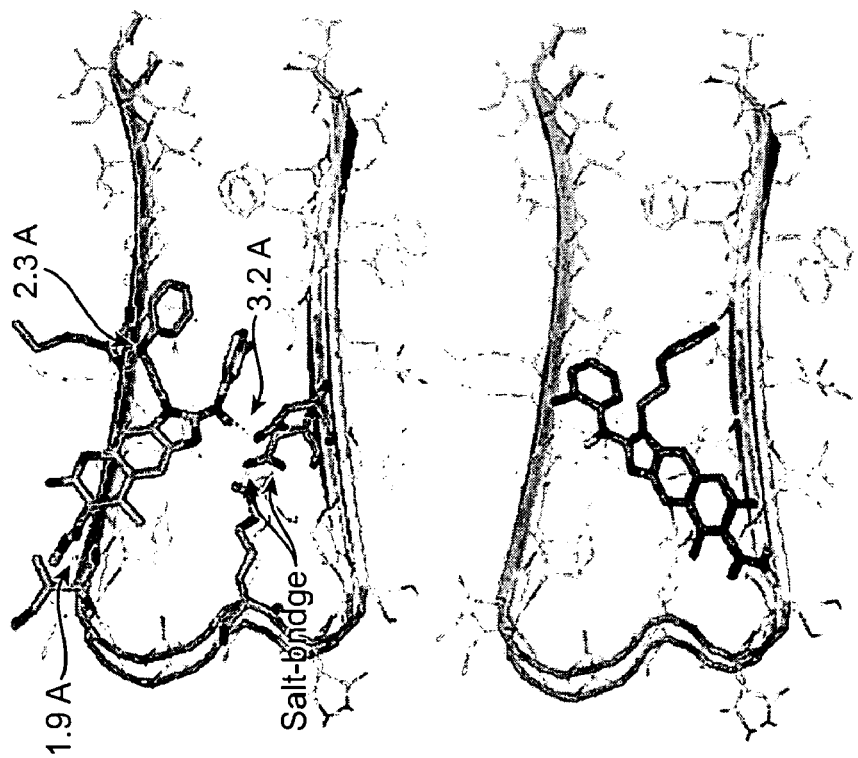
FIG. 9A
FIG. 9B

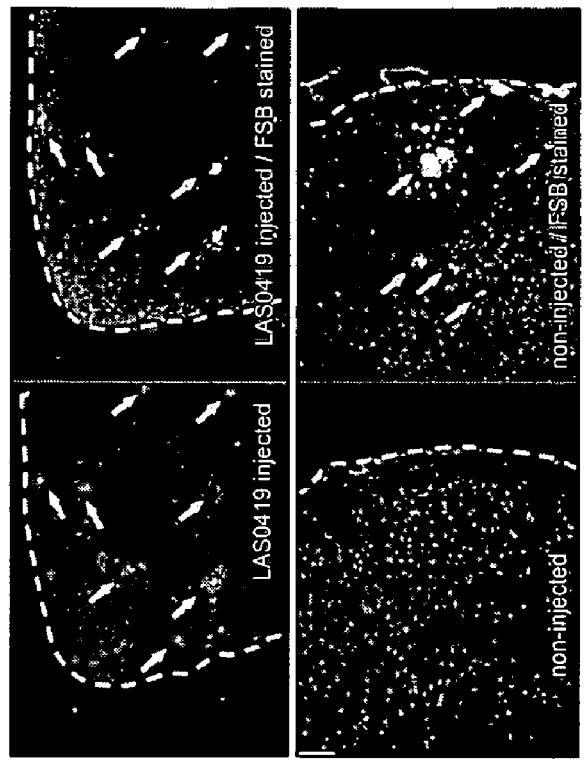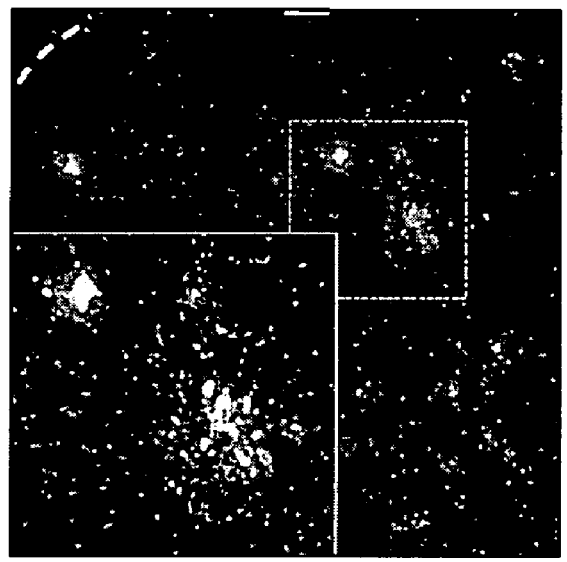

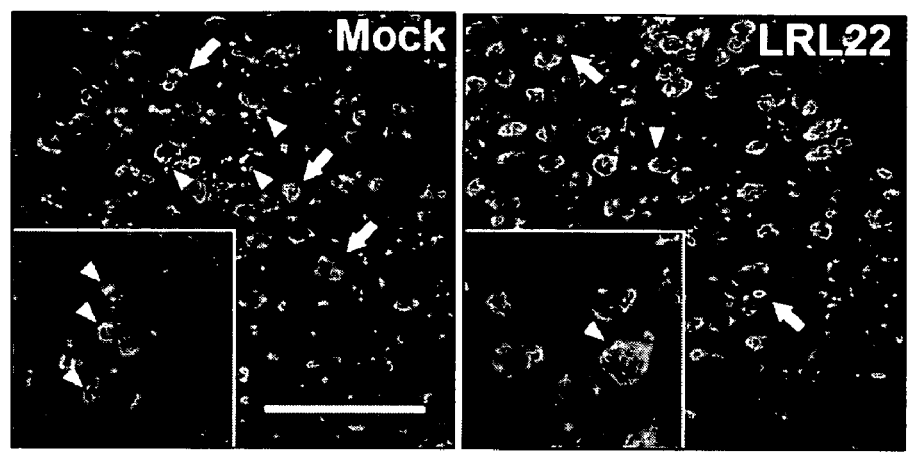
FIG. 12A
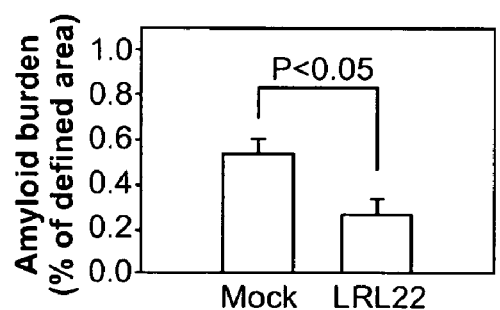 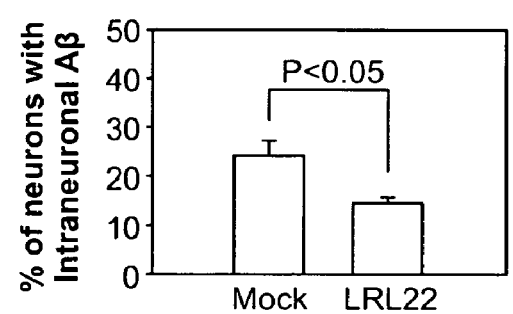
FIG. 12B
FIG. 12C

Aβ-BINDING SMALL MOLECULES

STATEMENT AS TO RIGHTS TO INVENTIONS MADE UNDER FEDERALLY SPONSORED RESEARCH AND DEVELOPMENT

Federally sponsored research or development money from NIH Grant No. 1R21 AG031362-01 was used in the development of this invention. The government may have right to aspects of this invention.

CROSS-REFERENCES TO RELATED APPLICATIONS

This application is the U.S. National Stage entry of International Application No. PCT/US2008/082096, filed Oct. 31, 2008, which claims priority to U.S. Application No. 60/985,138, filed Nov. 2, 2007, the disclosure of which is incorporated herein by reference in its entirety.

BACKGROUND OF THE INVENTION

Alzheimer's Disease (AD) is a degenerative brain disorder presented clinically by progressive loss of memory, cognition, reasoning, judgment, and emotional stability that gradually leads to profound mental deterioration and ultimately death. Individuals with AD exhibit characteristic β-amyloid deposits, i.e. β-amyloid plaques or fibrils, in the brain and in cerebral blood vessels, as well as neurofibrillary tangles in areas of the human brain important for memory and cognitive function, as determined during post-mortem analysis of AD patients' brains.

β-amyloid aggregates of different stages, ranging from fibrils (as seen in β-amyloid plaques), protofibrils, oligomers, amyloid pores, Aβ*56 and AD diffusible ligands (ADDL) are predominantly composed of β-amyloid peptides or fragments of β-amyloid peptides, including those ranging in length from 38-43 residues, i.e., $A\beta_{1-38}$, $A\beta_{1-39}$, $A\beta_{1-40}$, $A\beta_{1-42}$, $A\beta_{1-43}$ peptides, and fragments thereof, which are interchangeably referred to herein as AB peptides and Aβ peptides. The amino acid sequences of the Aβ peptides are known and differ only in the amino acids present at the C-terminus. For example, the sequence of the $A\beta_{1-42}$ and $A\beta_{1-43}$ differs from that of the $A\beta_{1-40}$ peptide by the addition of two and three, respectively, amino acids at the carboxyl (COOH) terminus.

Aβ peptide aggregate deposits (e.g., plaques) are also characterized in the brains of individuals with Down's Syndrome (Trisomy 21); mixed dementia, including those with combined AD and Parkinson's disease features and those with Lewy body diseases; cerebral amyloid angiopathy, Hereditary Cerebral Hemorrhage with Beta amyloidosis of the Dutch-Type, homozygotes for the apolipoprotein E4, inclusion body myosities, Niemann-Pick type C disease, and other such disorders.

In addition, there are many other forms of brain and non-brain amyloidosis in which the secondary structures of the amyloid are the same or similar. These amyloidosis include primary amyloidosis made of the amyloid light chain (AL) protein, secondary amyloidosis made of the amyloid-associated (AA) protein, hereditary forms of amyloidosis made of AA protein or amyloid transthyretin (ATTR), hemodialysis associated amyloidosis made of beta2-microglobulin, amyloid seen in diabetes made of islet amyloid polypeptide, prion amyloidosis in all kinds of prion disorders, alpha-synuclein amyloid inclusions in Parkinson's disease, amyloid neuropathy, and all other types of disorders labeled as "amyloidosis" or disorders with amyloid inclusions.

In reference to AD, presently, the prevailing "amyloid hypothesis" for AD holds that Aβ peptide monomers aggregate into self-assembled insoluble fibrillar deposits or plaques, and that these insoluble fibrils or plaque deposits are toxic to neuronal cells and is the pathological cause of AD. This theory was developed based, in part, from post-mortem analysis of AD patients' brain, when large numbers of these fibril or plaque deposits are found.

However, the amyloid hypothesis has been challenged by further clinical observations. For example, neuropathologists often observed a poor correlation between Aβ insoluble fibrils or plaque density with AD severity. Notably, there is poor correlation between the number, location and distribution of β-amyloid deposits in AD patients' brain, and parameter of AD pathology, including degree of dementia and neurodegeneration. More recent studies have suggested that soluble precursor Aβ peptide aggregates (e.g., Aβ oligomers (AβO) and Aβ protofibrils), which ultimately aggregate or "polymerize" to form insoluble Aβ deposits (e.g., plaques), are strong neurotoxins and may be the causative form of Aβ that is responsible for neuronal cell death in AD.

At present there are no effective treatments for preventing, or reversing the progression of Alzheimer's disease and treatment is primarily supportive. Stimulated memory exercises on a regular basis have been shown to slow, but not stop, memory loss. A few drugs, such as tacrine, result in a modest temporary improvement of cognition but do not stop the progression of dementia.

Presently, clinical diagnosis of AD is achieved mostly through clinical criteria evaluation, brain biopsies and post-mortem tissue studies. In particular, the inability to assess amyloid deposition in AD until after death impedes the study of this devastating illness. As it is likely that Aβ aggregation probably occurs long before clinical symptoms are noticeable and early detection and treatment of AD would delay the progression and the appearance of the most severe symptoms of the disease, it is generally recognized in the clinical community that a method of quantifying Aβ peptide aggregate deposits before death is needed both as a diagnostic tool in mild or clinically confusing cases, as well as, in monitoring the effectiveness of therapies targeted at preventing Aβ plaque deposition. Therefore, it remains of utmost importance to develop a safe and specific method for diagnosing AD before death by imaging Aβ peptide aggregate deposits in the brain in vivo.

Currently, there are no commercially available ante-mortem probes for detecting Aβ aggregates. Current research efforts to develop methods for diagnosing Alzheimer's disease ante-mortem in vivo have focused on genetic testing, immunoassay methods, and imaging techniques. It has been a challenge to develop high affinity probe for Aβ peptide aggregates that has low toxicity, can cross the blood-brain barrier, and binds more effectively to AD brain than to normal brain in order to identify AD related Aβ peptide aggregates deposits in brain before a patient's death.

In view of the above, there exists a need in the art for small-molecule therapeutic agents capable of preventing, slowing, or reversing the progression of Alzheimer's disease, such as, agents that block the toxic effects of Aβ peptide aggregates (e.g., AβO) on neuronal cells. Additionally, there exists a need for small-molecule ante-mortem probes for detecting Aβ aggregates that have low toxicity, can cross the blood-brain barrier, and binds with specificity to Aβ peptide aggregates, which can be used an ante-mortem probes for diagnosing AD in a person. The present invention satisfies these needs and provides additional advantages as well.

SUMMARY OF THE INVENTION

In one aspect, the present invention provides for a compound of Formula I:

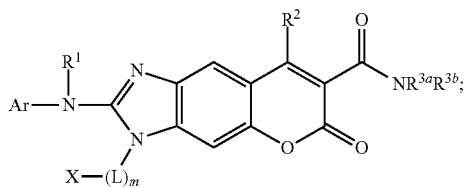

or a pharmaceutically acceptable salt thereof.

In Formula I, L is a linker selected from the group consisting of $C_{1-6}$ alkylene, $C_{1-6}$ heteroalkylene, $C_{2-6}$ alkenylene and $C_{2-6}$ alkynylene. The symbol X is a member selected from the group consisting of hydrogen, aryl, heteroaryl, $C_{3-10}$ cycloalkyl, $C_{3-9}$ heterocycloalkyl, $C_{1-6}$ alkyl, $C_{1-6}$ haloalkyl, wherein the X group is optionally substituted with 1 to 4 substituents selected from the group consisting of halogen, —$OR^a$, —$OC(O)R^b$, —$C(O)OR^a$, —$OC(O)NR^aR^b$, —$NR^aR^a$, —$C(O)NR^aR^a$, —CN, —$NO_2$, —$N_3$, —$NR^aC(O)R^b$, —$NR^aC(O)_2R^b$, —$SR^b$, —$S(O)R^b$, —$S(O)_2R^b$, —$NR^aS(O)_2R^b$, —$S(O)_2NR^aR^a$, —$NR^aS(O)_2R^b$ and —$NR^aS(O)_2NR^aR^a$, wherein any two substituents located on adjacent atoms on the X group is optionally combined to form a 5- to 8-membered ring. The $R^a$ substituent, at each occurrence, is independently selected from the group consisting of hydrogen, $C_{1-4}$ alkyl and $C_{1-4}$ heteroalkyl, and the substituent $R^b$ at each occurrence is independently selected from the group consisting of $C_{1-4}$ alkyl and $C_{1-4}$ heteroalkyl. When attached to the same nitrogen atom, $R^a$ and/or $R^b$ groups are optionally combined to form a 3- to 8-membered ring. In Formula I, Ar is a member selected from the group consisting of aryl ring system, heteroaryl ring system, $C_{3-10}$ cycloalkyl, $C_{3-9}$ heterocycloalkyl, $C_{1-6}$ alkyl and $C_{1-6}$ haloalkyl, and is optionally substituted with 1 to 4 substituents selected from the group consisting of -halogen, —CN, —$NO_2$, —$N_3$, —OR', —OC(O)R', —NR'R", —SR', —R', —$CO_2R'$, —CONR'R", —C(O)R', —OC(O)NR'R", —NR"C(O)R', —NR"C(O)_2R', —NR'—C(O)NR"R''', —NH—C(NH_2)=NH, —NR'C(NH_2)=NH, —NH—C(NH_2)=NR', —S(O)R', —S(O)_2R', —S(O)_2NR'R", —NR'S(O)_2R", perfluoro($C_1$-$C_4$)alkoxy, perfluoro($C_1$-$C_4$)alkyl, —$OR^c$, —$OC(O)R^d$, —$C(O)OR^c$, —$OC(O)NR^cR^d$, —$NR^cR^c$, —$C(O)NR^cR^c$, —$NR^cC(O)R^d$, —$NR^cC(O)_2R^d$, —$SR^d$, —$S(O)R^d$, —$S(O)_2R^d$, —$NR^cS(O)_2R^d$, —$S(O)_2NR^cR^c$, —$NR^cS(O)_2R^d$ and —$NR^cS(O)_2NR^cR^c$, where R', R" and R''' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl, and where $R^c$, at each occurrence, is independently selected from the group consisting of hydrogen, $C_{1-4}$ alkyl, $C_{1-4}$ heteroalkyl, $C_{3-10}$ cycloalkyl and $C_{3-9}$ heterocycloalkyl, and the substituent $R^d$ at each occurrence is independently selected from the group consisting of $C_{1-4}$ alkyl, $C_{1-4}$ heteroalkyl, $C_{3-10}$ cycloalkyl and $C_{3-9}$ heterocycloalkyl. Further when attached to the same nitrogen atom, $R^c$ and/or $R^d$ groups are optionally combined to form a 3- to 8-membered ring. In Formula I, $R^1$ is a member selected from the group consisting of hydrogen, $C_{1-6}$ alkyl and $C_{1-6}$ haloalkyl. The symbol $R^2$ is a member selected from the group consisting of hydrogen, halogen, $C_{1-6}$ alkoxy, $C_{1-6}$ alkylamino, $C_{1-6}$ dialkylamino, $C_{1-6}$ alkyl, $C_{1-6}$ haloalkyl, $C_{3-10}$ cycloalkyl and $C_{3-9}$ heterocycloalkyl. In Formula I, $R^{3a}$ and $R^{3b}$ are each a member independently selected from the group consisting of hydrogen, $C_{1-6}$ alkyl, $C_{1-6}$ haloalkyl, and $C_{1-6}$ alkoxy. $R^{3a}$ and $R^{3b}$, and the nitrogen atom to which each is attached, are optionally combined to form a 5- to 6-membered ring. In Formula I, the subscript m is the integer 0 or 1. For compounds of Formula I of the invention, there is the proviso that a compound of Formula I is not a compound selected from Table A.

In one embodiment, the present invention provides for a compound of Formula I, in which the symbol L is a linker selected from the group consisting of $C_{1-6}$ alkylene, $C_{1-6}$ heteroalkylene, $C_{2-6}$ alkenylene and $C_{2-6}$ alkynylene. The symbol X is a member selected from the group consisting of aryl, heteroaryl, $C_{3-10}$ cycloalkyl, $C_{3-9}$ heterocycloalkyl, $C_{1-6}$ alkyl, $C_{1-6}$ haloalkyl, wherein the X group is optionally substituted with 1 to 4 substituents selected from the group consisting of halogen, —$OR^a$, —$OC(O)R^b$, —$C(O)OR^a$, —$OC(O)NR^aR^b$, —$NR^aR^a$, —$C(O)NR^aR^a$, —CN, —$NO_2$, —$N_3$, —$NR^aC(O)R^b$, —$NR^aC(O)_2R^b$, —$SR^b$, —$S(O)R^b$, —$S(O)_2R^b$, —$NR^aS(O)_2R^b$, —$S(O)_2NR^aR^a$, —$NR^aS(O)_2R^b$ and —$NR^aS(O)_2NR^aR^a$. Any two substituents located on adjacent atoms on the X group is optionally combined to form a 5- to 8-membered ring. The $R^a$ substituent, at each occurrence, is independently selected from the group consisting of hydrogen, $C_{1-4}$ alkyl and $C_{1-4}$ heteroalkyl, and the $R^b$ substituent at each occurrence is independently selected from the group consisting of $C_{1-4}$ alkyl and $C_{1-4}$ heteroalkyl. When attached to the same nitrogen atom, $R^a$ and/or $R^b$ substituents are optionally combined to form a 3- to 8-membered ring. In Formula I, Ar represents an aryl or heteroaryl ring system, and is optionally substituted with 1 to 4 substituents selected from the group consisting of -halogen, —CN, —$NO_2$, —$N_3$, —OR', —OC(O)R', —NR'R", —SR', —R', —$CO_2R'$, —CONR'R", —C(O)R', —OC(O)NR'R", —NR"C(O)R', —NR"C(O)_2R', —NR'—C(O)NR"R''', —NH—C(NH_2)=NH, —NR'C(NH_2)=NH, —NH—C(NH_2)=NR', —S(O)R', —S(O)_2R', —S(O)_2NR'R", —NR'S(O)_2R", perfluoro($C_1$-$C_4$)alkoxy, perfluoro($C_1$-$C_4$)alkyl, —$OR^c$, —$OC(O)R^d$, —$C(O)OR^c$, —$OC(O)NR^cR^d$, —$NR^cR^c$, —$C(O)NR^cR^c$, —$NR^cC(O)R^d$, —$NR^cC(O)_2R^d$, —$SR^d$, —$S(O)R^d$, —$S(O)_2R^d$, —$NR^cS(O)_2R^d$, —$S(O)_2NR^cR^c$, —$NR^cS(O)_2R^d$ and —$NR^cS(O)_2NR^cR^c$, where R', R" and R''' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl, and wherein the $R^c$ substituent, at each occurrence, is independently selected from the group consisting of hydrogen, $C_{1-4}$ alkyl and $C_{1-4}$ heteroalkyl. The $R^d$ substituents at each occurrence is independently selected from the group consisting of $C_{1-4}$ alkyl and $C_{1-4}$ heteroalkyl. When attached to the same nitrogen atom, the $R^c$ and/or $R^d$ are optionally combined to form a 3- to 8-membered ring. In Formula I, $R^1$ is a member selected from the group consisting of hydrogen, $C_{1-6}$ alkyl and $C_{1-6}$ haloalkyl; $R^2$ is a member selected from the group consisting of hydrogen, halogen, $C_{1-6}$ alkoxy, $C_{1-6}$ alkylamino, $C_{1-6}$ dialkylamino, $C_{1-6}$ alkyl and $C_{1-6}$ haloalkyl; and $R^{3a}$ and $R^{3b}$ are each a member independently selected from the group consisting of hydrogen, $C_{1-6}$ alkyl, $C_{1-6}$ haloalkyl, and $C_{1-6}$ alkoxy. Moreover, in Formula I, $R^{3a}$ and $R^{3b}$ and the nitrogen atom to which each is attached are optionally combined to form a 5- to 6-membered ring. The subscript m is the integer 0 or 1. For compounds of Formula I there is the proviso that the compound is not a compound selected from Table A.

In another aspect, the present invention provides for labeled compound of Formula I.

In another aspect, the present invention provides for various method for using compounds and labeled compounds of Formula I for therapeutic and imaging applications. In one embodiment, compounds and labeled compounds of Formula I are effective at binding to Aβ peptide aggregates (e.g., AβO, fibrils, plaques). In another embodiment of the invention, compounds and labeled compounds of Formula I can reduce the size or prevent the growth of Aβ peptide aggregates (e.g., AβO, fibrils, plaques) in a patient. In another embodiment, compounds and labeled compounds of Formula I are effective to prevent the binding of Aβ peptide aggregates to synapses in a patient. In another embodiment, the present invention provides for compounds and labeled compounds of Formula I for the treatment of diseases caused by Aβ peptide aggregation or deposition, e.g., Alzheimer's disease, in a patient. In yet another embodiment, compounds or labeled compounds of Formula I are useful as biomedical probes for in vivo or in vitro imaging of Aβ peptide aggregates. In another embodiment, radioactive compounds of Formula I are useful as biomedical probes for in vivo or in vitro imaging of Aβ peptide aggregates.

BRIEF DESCRIPTION OF THE DRAWINGS

FIG. 6 relates to the synaptic binding assay data obtained for compounds of the invention. LAS0419 is Compound A of FIG. 1. CR is Congo Red.

FIG. 9A and FIG. 9B provide the molecular modeling results obtained for isomeric compounds of the invention.

FIG. 11A and FIG. 11B relates to the in vivo assay results obtained for compounds of the invention. LAS0419 is Compound A of FIG. 1. FIG. 11C shows results for a control.

FIG. 12 shows compound A reduces the Ab deposition in vivo. Compound A (5.3 mg/g body weight) or the solvent for compound A (mock) was IP injected daily into a robust Alzheimer model 5xFAD mice, starting at 2 months of age and for a 3-week period. n=4 per group. (A) The sections were stained with the specific antibody for the long form of Aβ called Aβ-42 (red) and for the neuronal marker NeuN (green nuclear stain). Shown are representative images from subiculum, where amyloid deposits were most abundant. Scale bar: 100 mm. Arrows: extracellular plaques; arrowheads: neurons with intraneuronal Aβ42, which are better illustrated in magnified images in insets. (B) The amyloid burden is quantified as the % area occupied by plaques in a separate set of sections stained by FSB. FSB is an amyloid dye that does not stain intraneuronal Aβ. (C) The abundance of intraneuronal Aβ was quantified by counting the number of NeuN-positive neurons in subiculum with intraneuronal Aβ. Overall, ~250 neurons were counted. Student's t-test showed significant reductions of both extracellular plaques and intraneuronal Aβ after compound A treatment. The results show that a 3-week treatment of mice with compound A significantly reduced the amyloid load, both in the form of extracellular amyloid plaques and intraneuronal Aβ. LRL22 is Compound A of FIG. 1.

DETAILED DESCRIPTION OF THE INVENTION

I. Abbreviation and Definitions

Figure 1:
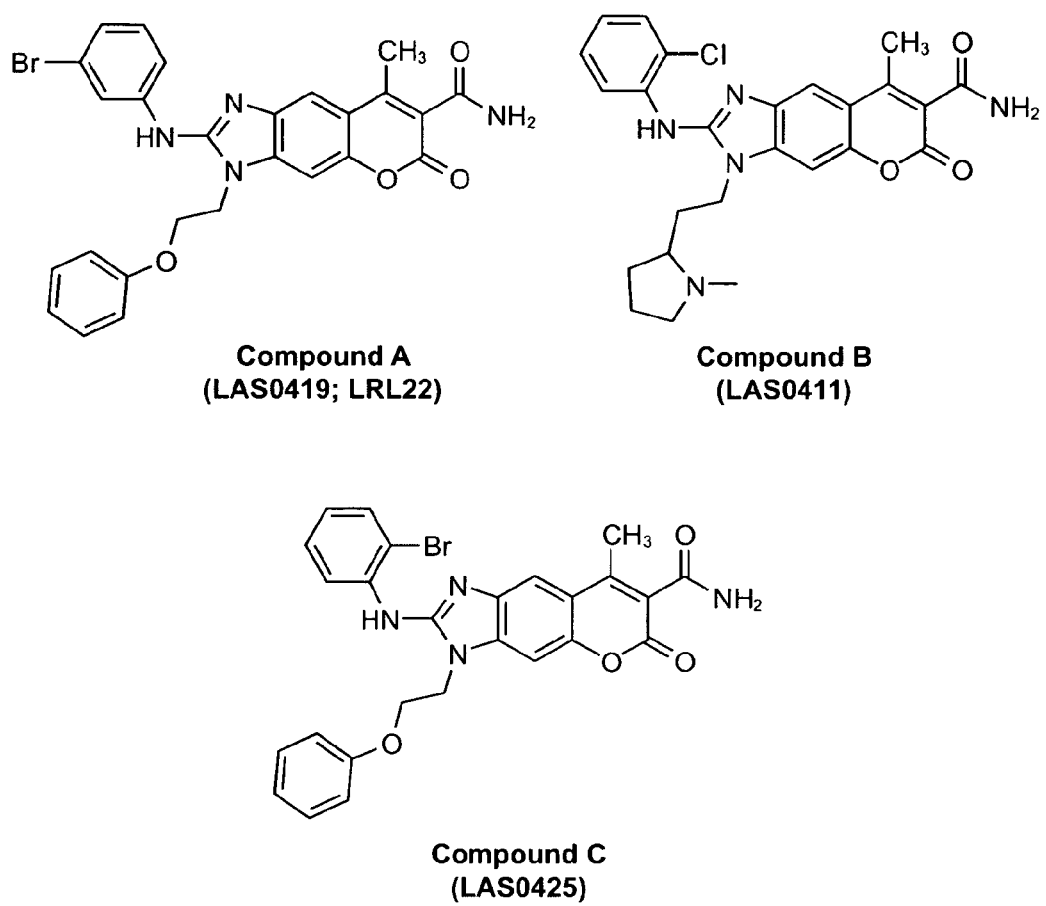
FIG. 1 provides the structure of Compounds A, B and C of the invention.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "cycloalkyl" refers to hydrocarbon rings having the indicated number of carbon ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group having the number of carbon atoms stated and that further contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$.

The term "alkylene" by itself or as part of another substituent means a divalent radical derived from an alkane, as exemplified by —$CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl, unless otherwise stated, will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from, for example, -halogen, —OR', —NR'R'', —SR', —SiR'R''R''', —OC(O)R', —C(O)R', —$CO_2$R', —CONR'R'', —OC(O)NR'R'', —NR''C(O)R', —NR'—C(O)NR''R''', —NR''C(O)$_2$R', —NH—C($NH_2$)=NH, —NR'C($NH_2$)=NH, —NH—C($NH_2$)=NR', —S(O)R', —S(O)$_2$R', —S(O)$_2$NR'R'', —NR'S(O)$_2$R'', —CN and —$NO_2$, among others, in a number ranging from zero to (2 m'+1), where m' is the total number of carbon atoms in such radical. R', R'' and R''' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R'' are attached to the same nitrogen atom, they can be combined with the nitrogen atom to form a 3-, 4-, 5-, 6-, or 7-membered ring. For example, —NR'R'' is meant to include 1-pyrrolidinyl and 4-morpholinyl.

Similarly, substituents for the aryl and heteroaryl groups are varied and are generally selected from, for example, -halogen, —OR', —OC(O)R', —NR'R'', —SR', —R', —CN, —$NO_2$, —$CO_2$R', —CONR'R'', —C(O)R', —OC(O)NR'R'', —NR''C(O)R', —NR''C(O)$_2$R', —NR'—C(O)NR''R''', —NH—C($NH_2$)=NH, —NR'C($NH_2$)=NH, —NH—C($NH_2$)=NR', —S(O)R', —S(O)$_2$R', —S(O)$_2$NR'R'', —NR'S(O)$_2$R'', —$N_3$, perfluoro($C_1$-$C_4$)alkoxy, perfluoro($C_1$-$C_4$) alkyl, among others, in a number ranging from zero to the total number of open valences on the aromatic ring system; and where R', R'' and R''' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-($CH_2$)$_r$—B—, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)ₛ—X—(CH₂)ₜ—, where s and t are independently integers of from 0 to 3, and X is —O—, —NR'—, —S—, —S(O)—, —S(O)₂—, or —S(O)₂NR'—. The substituent R' in —NR'— and —S(O)₂NR'— is selected from hydrogen or unsubstituted C₁₋₆ alkyl.

As used herein, the term "Aβ peptide aggregates" refers to Aβ peptides at various stages of aggregation, e.g., oligomers, protofibrils, fibrils (as seen in β-amyloid plaques), amyloid pores, Ab*56, and AD diffusible ligands (ADDL); which are predominantly composed of β-amyloid peptides of fragments of β-amyloid peptides, including peptides in the range from 38-43 residues, i.e., Aβ₁₋₃₈, Aβ₁₋₃₉, Aβ₁₋₄₀, Aβ₁₋₄₂, Aβ₁₋₄₃ and fragments thereof.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention contain atomic isotopes at one or more of the atoms that constitute such compounds in their natural proportions. For example, the compounds naturally occurring stable isotopes, such as, for example, carbon-13 ($^{13}$C).

II. Compounds and Labeled Compounds

In one aspect, the present invention provides for compounds that bind to Aβ peptide aggregates, e.g., oligomers, protofibrils, fibrils and plaques, amyloid pores, Aβ*56, AD diffusible ligands (ADDL). The compounds of the invention are of Formula I.

The present invention provides for a compound of Formula I:

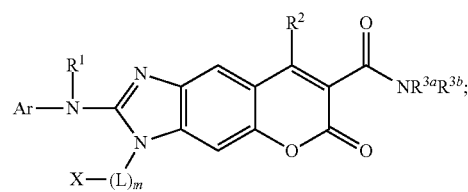

or a pharmaceutically acceptable salt thereof.

In Formula I, L is a linker selected from the group consisting of C₁₋₆ alkylene, C₁₋₆ heteroalkylene, C₂₋₆ alkenylene and C₂₋₆ alkynylene. The symbol X is a member selected from the group consisting of hydrogen, aryl, heteroaryl, C₃₋₁₀ cycloalkyl, C₃₋₉ heterocycloalkyl, C₁₋₆ alkyl, C₁₋₆ haloalkyl, wherein the X group is optionally substituted with 1 to 4 substituents selected from the group consisting of halogen, —ORᵃ, —OC(O)Rᵇ, —C(O)ORᵃ, —OC(O)NRᵃRᵇ, —NRᵃRᵃ, —C(O)NRᵃRᵃ, —CN, —NO₂, —N₃, —NRᵃC(O) Rᵇ, —NRᵃC(O)₂Rᵇ, —SRᵇ, —S(O)Rᵇ, —S(O)₂Rᵇ, —NRᵃS (O)₂Rᵇ, —S(O)₂NRᵃRᵃ, —NRᵃS(O)₂Rᵇ and —NRᵃS(O)₂ NRᵃRᵃ, wherein any two substituents located on adjacent atoms on the X group is optionally combined to form a 5-to 8-membered ring. The Rᵃ substituent, at each occurrence, is independently selected from the group consisting of hydrogen, C₁₋₄ alkyl and C₁₋₄ heteroalkyl, and the substituent Rᵇ at each occurrence is independently selected from the group consisting of $C_{1-4}$ alkyl and $C_{1-4}$ heteroalkyl. When attached to the same nitrogen atom, $R^a$ and/or $R^b$ groups are optionally combined to form a 3- to 8-membered ring. In Formula I, Ar is a member selected from the group consisting of aryl ring system, heteroaryl ring system, $C_{3-10}$ cycloalkyl, $C_{3-9}$ heterocycloalkyl, $C_{1-6}$ alkyl and $C_{1-6}$ haloalkyl, and is optionally substituted with 1 to 4 substituents selected from the group consisting of -halogen, —CN, —NO$_2$, —N$_3$, —OR', —OC(O)R', —NR'R", —SR', —R', —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", perfluoro($C_1$-$C_4$)alkoxy, perfluoro($C_1$-$C_4$)alkyl, —OR$^c$, —OC(O)R$^d$, —C(O)OR$^c$, —OC(O)NR$^c$R$^d$, —NR$^c$R$^c$, —C(O)NR$^c$R$^c$, —NR$^c$C(O)R$^d$, —NR$^c$C(O)$_2$R$^d$, —SR$^d$, —S(O)R$^d$, —S(O)$_2$R$^d$, —NR$^c$S(O)$_2$R$^d$, —S(O)$_2$NR$^c$R$^c$, —NR$^c$S(O)$_2$R$^d$ and —NR$^c$S(O)$_2$NR$^c$R$^c$, where R', R" and R"' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl, and where R$^c$, at each occurrence, is independently selected from the group consisting of hydrogen, $C_{1-4}$ alkyl, $C_{1-4}$ heteroalkyl, $C_{3-10}$ cycloalkyl and $C_{3-9}$ heterocycloalkyl, and the substituent R$^d$ at each occurrence is independently selected from the group consisting of $C_{1-4}$ alkyl, $C_{1-4}$ heteroalkyl, $C_{3-10}$ cycloalkyl and $C_{3-9}$ heterocycloalkyl. Further when attached to the same nitrogen atom, R$^c$ and/or R$^d$ groups are optionally combined to form a 3- to 8-membered ring. In Formula I, $R^1$ is a member selected from the group consisting of hydrogen, $C_{1-6}$ alkyl and $C_{1-6}$ haloalkyl. The symbol $R^2$ is a member selected from the group consisting of hydrogen, halogen, $C_{1-6}$ alkoxy, $C_{1-6}$ alkylamino, $C_{1-6}$ dialkylamino, $C_{1-6}$ alkyl, $C_{1-6}$ haloalkyl, $C_{3-10}$ cycloalkyl and $C_{3-9}$ heterocycloalkyl. The substituents $R^{3a}$ and $R^{3b}$ are each a member independently selected from the group consisting of hydrogen, $C_{1-6}$ alkyl, $C_{1-6}$ haloalkyl, and $C_{1-6}$ alkoxy. $R^{3a}$ and $R^{3b}$, and the nitrogen atom to which each is attached, are optionally combined to form a 5- to 6-membered ring. In Formula I, the subscript m is the integer 0 or 1. For compounds of Formula I of the invention, there is the proviso that a compound of Formula I is not a compound selected from Table A.

In some embodiments, Ar is a member selected from the group consisting of aryl ring system, heteroaryl ring system, $C_{3-10}$ cycloalkyl, $C_{3-9}$ heterocycloalkyl, $C_{1-6}$ alkyl and $C_{1-6}$ haloalkyl, and is optionally substituted with 1 to 4 substituents selected from the group consisting of halogen, —OR$^c$, —OC(O)R$^d$, —C(O)OR$^c$, —OC(O)NR$^c$R$^d$, —NR$^c$R$^c$, —C(O)NR$^c$R$^c$, —CN, —NO$_2$, —N$_3$, —NR$^c$C(O)R$^d$, —NR$^c$C(O)$_2$R$^d$, —SR$^d$, —S(O)R$^d$, —S(O)$_2$R$^d$, —NR$^c$S(O)$_2$R$^d$, —S(O)$_2$NR$^c$R$^c$, —NR$^c$S(O)$_2$R$^d$ and —NR$^c$S(O)$_2$NR$^c$R$^c$. The substituent R$^c$, at each occurrence, is independently selected from the group consisting of hydrogen, $C_{1-4}$ alkyl, $C_{1-4}$ heteroalkyl, $C_{3-10}$ cycloalkyl and $C_{3-9}$ heterocycloalkyl, and the substituent R$^d$ at each occurrence is independently selected from the group consisting of $C_{1-4}$ alkyl, $C_{1-4}$ heteroalkyl, $C_{3-10}$ cycloalkyl and $C_{3-9}$ heterocycloalkyl. Further when attached to the same nitrogen atom, R$^c$ and/or R$^d$ groups are optionally combined to form a 3- to 8-membered ring.

In one embodiment, in compounds of Formula I, the symbol L is a linker selected from the group consisting of $C_{1-6}$ alkylene, $C_{1-6}$ heteroalkylene, $C_{2-6}$ alkenylene and $C_{2-6}$ alkynylene. The symbol X is a member selected from the group consisting of aryl, heteroaryl, $C_{3-10}$ cycloalkyl, $C_{3-9}$ heterocycloalkyl, $C_{1-6}$ alkyl, $C_{1-6}$ haloalkyl, wherein the X group is optionally substituted with 1 to 4 substituents selected from the group consisting of halogen, —OR$^a$, —OC(O)R$^b$, —C(O)OR$^a$, —OC(O)NR$^a$R$^b$, —NR$^a$R$^a$, —C(O)NR$^a$R$^a$, —CN, —NO$_2$, —N$_3$, —NR$^a$C(O)R$^b$, —NR$^a$C(O)$_2$R$^b$, —SR$^b$, —S(O)R$^b$, —S(O)$_2$R$^b$, —NR$^a$S(O)$_2$R$^b$, —S(O)$_2$NR$^a$R$^a$, —NR$^a$S(O)$_2$R$^b$ and —NR$^a$S(O)$_2$NR$^a$R$^a$. Any two substituents located on adjacent atoms on the X group is optionally combined to form a 5- to 8-membered ring. The R$^a$ substituent, at each occurrence, is independently selected from the group consisting of hydrogen, $C_{1-4}$ alkyl and $C_{1-4}$ heteroalkyl, and the R$^b$ substituent at each occurrence is independently selected from the group consisting of $C_{1-4}$ alkyl and $C_{1-4}$ heteroalkyl. When attached to the same nitrogen atom, R$^a$ and/or R$^b$ substituents are optionally combined to form a 3- to 8-membered ring. In Formula I, Ar represents an aryl or heteroaryl ring system, and is optionally substituted with 1 to 4 substituents selected from the group consisting of -halogen, —CN, —NO$_2$, —N$_3$, —OR', —OC(O)R', —NR'R", —SR', —R', —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", perfluoro($C_1$-$C_4$)alkoxy, perfluoro($C_1$-$C_4$)alkyl, —OR$^c$, —OC(O)R$^d$, —C(O)OR$^c$, —OC(O)NR$^c$R$^d$, —NR$^c$R$^c$, —C(O)NR$^c$R$^c$, —NR$^c$C(O)R$^d$, —NR$^c$C(O)$_2$R$^d$, —SR$^d$, —S(O)R$^d$, —S(O)$_2$R$^d$, —NR$^c$S(O)$_2$R$^d$, —S(O)$_2$NR$^c$R$^c$, —NR$^c$S(O)$_2$R$^d$ and —NR$^c$S(O)$_2$NR$^c$R$^c$, where R', R" and R"' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl, and wherein the R$^c$ substituent, at each occurrence, is independently selected from the group consisting of hydrogen, $C_{1-4}$ alkyl and $C_{1-4}$ heteroalkyl. The R$^d$ substituents at each occurrence is independently selected from the group consisting of $C_{1-4}$ alkyl and $C_{1-4}$ heteroalkyl. When attached to the same nitrogen atom, the R$^c$ and/or R$^d$ are optionally combined to form a 3- to 8-membered ring. In Formula I, $R^1$ is a member selected from the group consisting of hydrogen, $C_{1-6}$ alkyl and $C_{1-6}$ haloalkyl; $R^2$ is a member selected from the group consisting of hydrogen, halogen, $C_{1-6}$ alkoxy, $C_{1-6}$ alkylamino, $C_{1-6}$ dialkylamino, $C_{1-6}$ alkyl and $C_{1-6}$ haloalkyl; and $R^{3a}$ and $R^{3b}$ are each a member independently selected from the group consisting of hydrogen, $C_{1-6}$ alkyl, $C_{1-6}$ haloalkyl, and $C_{1-6}$ alkoxy. Moreover, in Formula I, $R^{3a}$ and $R^{3b}$ and the nitrogen atom to which each is attached are optionally combined to form a 5- to 6-membered ring. The subscript m is the integer 0 or 1. For compounds of Formula I, there is the proviso that the compound is not a compound selected from Table A.

In some embodiments, Ar represents an aryl or heteroaryl ring system, and is optionally substituted with 1 to 4 substituents selected from the group consisting of -halogen, —CN, —NO$_2$, —N$_3$, —OR', —OC(O)R', —NR'R", —SR', —R', —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", perfluoro($C_1$-$C_4$)alkoxy, perfluoro($C_1$-$C_4$)alkyl, —OR$^c$, —OC(O)R$^d$, —C(O)OR$^c$, —OC(O)NR$^c$R$^d$, —NR$^c$R$^c$, —C(O)NR$^c$R$^c$, —NR$^c$C(O)R$^d$, —NR$^c$C(O)$_2$R$^d$, —SR$^d$, —S(O)R$^d$, —S(O)$_2$R$^d$, —NR$^c$S(O)$_2$R$^d$, —S(O)$_2$NR$^c$R$^c$, —NR$^c$S(O)$_2$R$^d$ and —NR$^c$S(O)$_2$NR$^c$R$^c$, where R', R" and R"' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl.

In some other embodiments, Ar represents an aryl or heteroaryl ring system, and is optionally substituted with 1 to 4 substituents selected from the group consisting of halogen, —OR$^c$, —OC(O)R$^d$, —C(O)OR$^c$, —OC(O)NR$^c$R$^c$, —NR$^c$R$^c$, —C(O)NR$^c$R$^c$, —CN, —NO$_2$, —N$_3$, —NR$^c$C(O)R$^d$, —NR$^c$C(O)$_2$R$^d$, —SR$^d$, —S(O)R$^d$, —S(O)$_2$R$^d$, —NR$^c$S(O)$_2$R$^d$, —S(O)$_2$NR$^c$R$^c$, —NR$^c$S(O)$_2$R$^d$ and —NR$^c$S(O)$_2$NR$^c$R$^c$, wherein the R$^c$ substituent, at each occurrence, is independently selected from the group consisting of hydrogen, C$_{1-4}$ alkyl and C$_{1-4}$ heteroalkyl. The R$^d$ substituents at each occurrence is independently selected from the group consisting of C$_{1-4}$ alkyl and C$_{1-4}$ heteroalkyl. When attached to the same nitrogen atom, the R$^c$ and/or R$^d$ are optionally combined to form a 3-to 8-membered ring.

In one embodiment of Formula I, L is selected from C$_{1-6}$ alkylene and C$_{1-6}$ heteroalkylene. In another embodiment of Formula I, L is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$O—, —CH$_2$CH$_2$NH—, —CH$_2$CH$_2$CH$_2$O—, —CH$_2$CH$_2$CH$_2$NH—, —CH$_2$OCH$_2$CH$_2$— and —CH$_2$NHCH$_2$CH$_2$—; R$^1$ is selected from the group consisting of hydrogen, methyl, ethyl and propyl; R$^2$ is selected from the group consisting of hydrogen, methoxy, ethoxy, methylamino, ethylamino, dimethylamino, diethylamino, methyl, ethyl, propyl and trifluoromethyl; and R$^{3a}$ and R$^{3b}$ are each independently selected from the group consisting of hydrogen, methyl, ethyl, methoxy and ethoxy, wherein R$^{3a}$ and R$^{3b}$ and the nitrogen atom to which each is attached are optionally combined to form a 5-to 6-membered ring. Within one aspect of this embodiment, in certain instances, L is selected from the group consisting of —CH$_2$—, —CH$_2$CH$_2$—, —CH$_2$CH$_2$CH$_2$—, —CH$_2$CH$_2$O— and —CH$_2$CH$_2$NH—.

In another embodiment of Formula I, X is selected from the group consisting of optionally substituted aryl, heteroaryl, C$_{3-10}$ cycloalkyl and C$_{3-9}$ heterocycloalkyl; L is a linker selected from the group consisting of C$_{1-6}$ alkylene and C$_{1-6}$ heteroalkylene; and the subscript m is the integer 1. In certain aspects of this embodiment, X is selected from the group consisting of optionally substituted phenyl, naphthyl, pyridyl, quinolinyl, pyrazinyl, pyrazolyl, benzopyrazoloyl, imidazolyl, benzimidazolyl, furanyl, benzofuranyl, isoxazolyl, oxazolyl, azepanyl, piperidinyl, pyrrolidinyl, azetidinyl, tetrahydrofuranyl, tetrahydropyranyl, valerolactamyl, butyrolactamyl, caprolactamyl, butyrolactonyl, gamma-lactonyl, delta-lactonyl, cyclopropyl, cyclopentyl, cyclohexyl, morpholinyl, thiomorpholinyl and piperazinyl. In some cases, X is selected from the group consisting of phenyl, naphthyl, piperidinyl, pyrrolidinyl, morpholinyl, thiomorpholinyl and piperazinyl.

In another embodiment, in compounds of Formula I, the X-(L)$_m$-group is selected from the group consisting of:

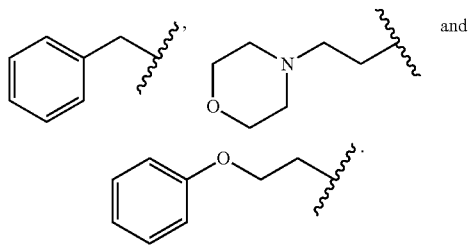

In other embodiments, in compounds of Formula I, the X-(L)$_m$-group is selected from the group consisting of:

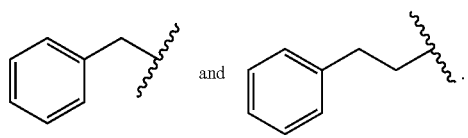

In some embodiments, X is phenyl substituted with 1 to 4 substituents selected from the group consisting of halogen, —OR$^a$, —OC(O)R$^b$, —C(O)OR$^a$, —OC(O)NR$^a$R$^b$, —NR$^a$R$^a$, —C(O)NR$^a$R$^a$, —CN, —NO$_2$, —N$_3$, —NR$^a$C(O)R$^b$, —NR$^a$C(O)$_2$R$^b$, —SR$^b$, —S(O)R$^b$, —S(O)$_2$R$^b$, —NR$^a$S(O)$_2$R$^b$, —S(O)$_2$NR$^a$R$^a$, —NR$^a$S(O)$_2$R$^b$ and —NR$^a$S(O)$_2$NR$^a$R$^a$. In another embodiment, X is phenyl substituted with halogen. In some other embodiments, X is phenyl substituted with a member selected from the group consisting of Cl, Br and I.

In another embodiment, in compounds of Formula I, X is selected from the group consisting of optionally substituted C$_{1-6}$ alkyl and C$_{1-6}$ haloalkyl; and L is a linker selected from the group consisting of C$_{1-6}$ alkylene and C$_{1-6}$ heteroalkylene. Within this embodiment, in certain cases, X is selected from the group consisting of methyl, ethyl, n-propyl, iso-propyl, butyl, sec-butyl, iso-butyl and tert-butyl.

In another embodiment, in compounds of Formula I, Ar is selected from the group consisting of phenyl, pyridyl or naphthyl and is optionally substituted with 1 to 3 substituents selected from the group consisting of halogen, —OR$^c$, —NR$^c$R$^c$, —CN, —NO$_2$, —N$_3$, and —SR$^d$. Within certain aspects of this embodiment, Ar is a 3-substituted phenyl ring. In some embodiments, Ar is phenyl substituted with perfluoro(C$_1$-C$_4$) alkoxy. In other embodiments, Ar is phenyl substituted with trifluoromethoxy. In some other embodiments, Ar is phenyl substituted with —OR$^c$, wherein R$^c$ is C$_{1-4}$ alkyl. In still other embodiments, Ar is phenyl substituted with methoxy.

In another embodiment, in compounds of Formula I, Ar is selected from the group consisting of:

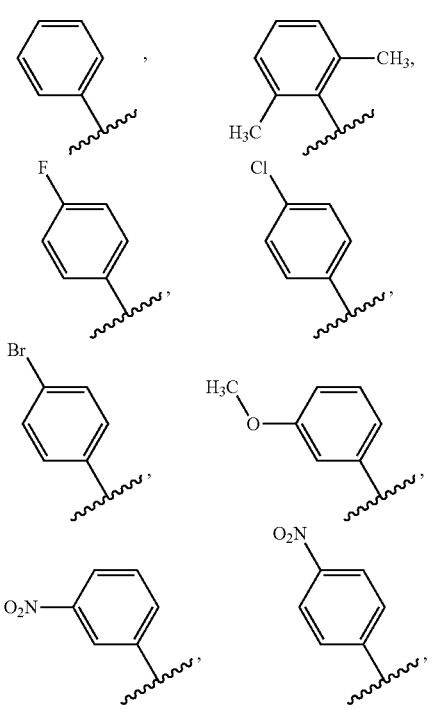

-continued

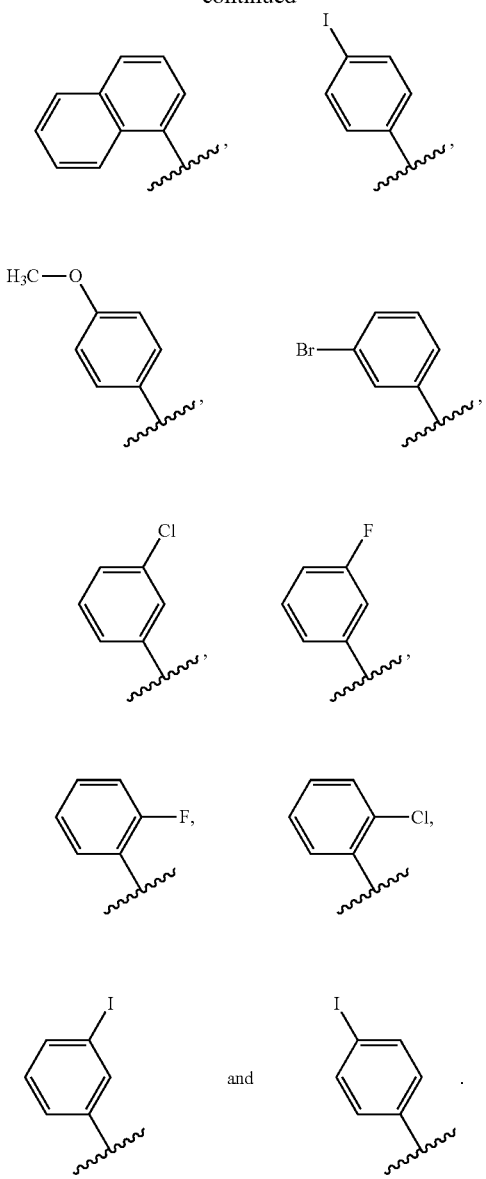

Within certain aspects of the above embodiment, Ar is selected from the group consisting of:

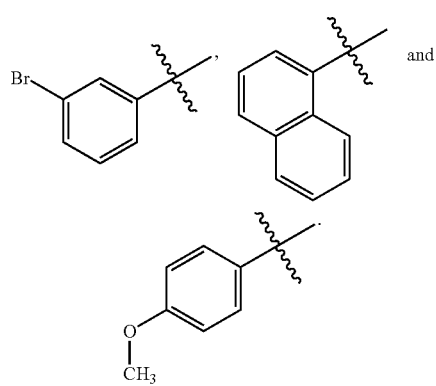

In some embodiments, Ar is selected from the group consisting of:

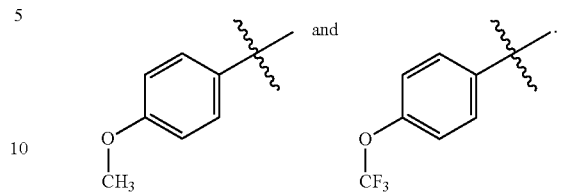

In another embodiment, Ar is selected from $C_{3-10}$ cycloalkyl, $C_{3-9}$ heterocycloalkyl, $C_{1-6}$ alkyl and $C_{1-6}$ haloalkyl. In one aspect of this embodiment, Ar is selected from the group consisting of methyl, ethyl, propyl and isopropyl. In one embodiment Ar is propyl or butyl.

In another embodiment, compounds of Formula I are of the sub-formula Ia.

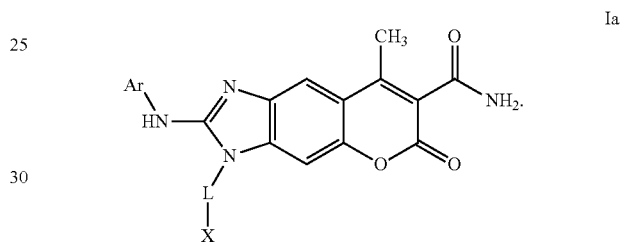

In yet another embodiment, compounds of Formula I are selected from the group of compounds presented in Table B and Table C.

In some embodiments, the compound is selected from the group consisting of:

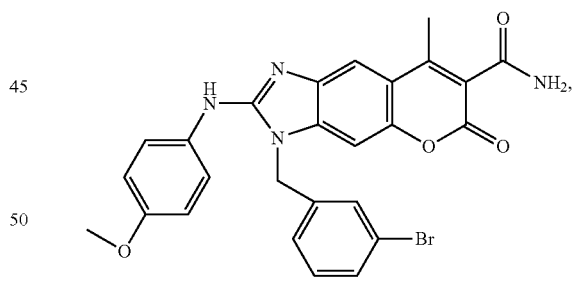

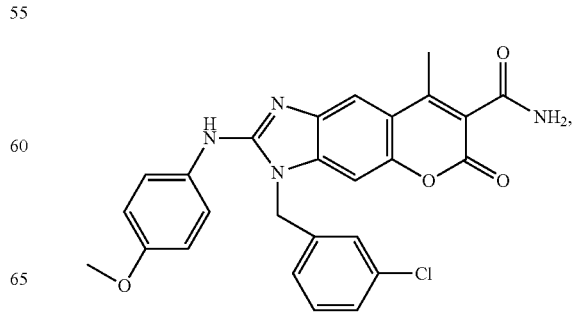

-continued
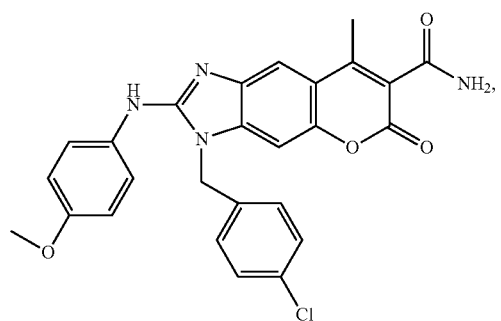
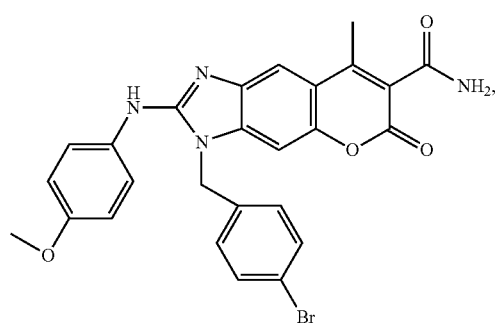
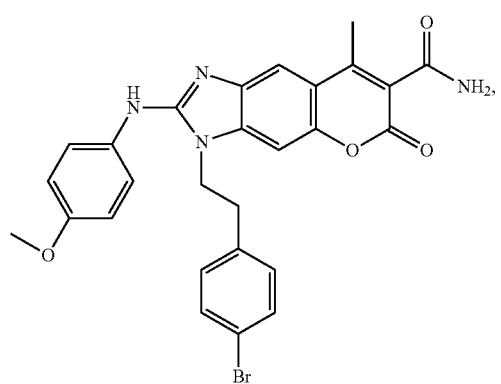
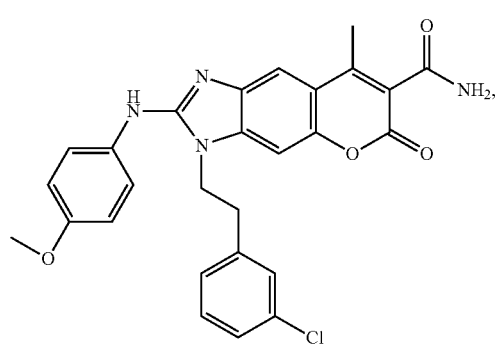
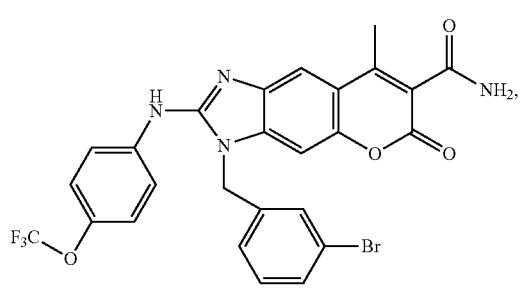
-continued
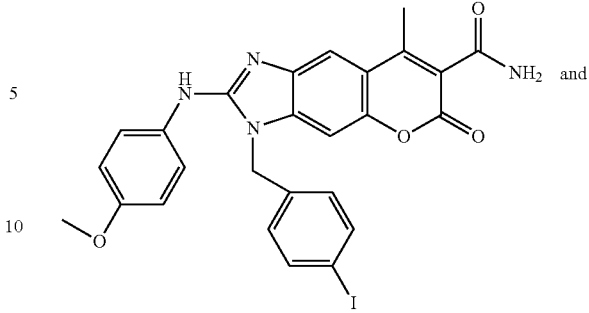
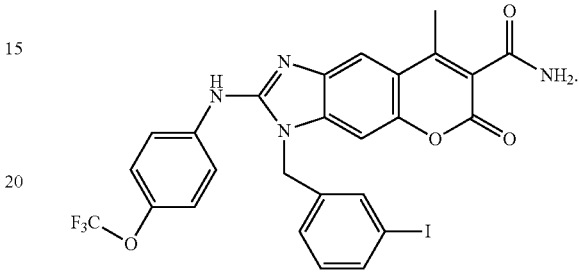
In some other embodiments, the compound is selected from the group consisting of:
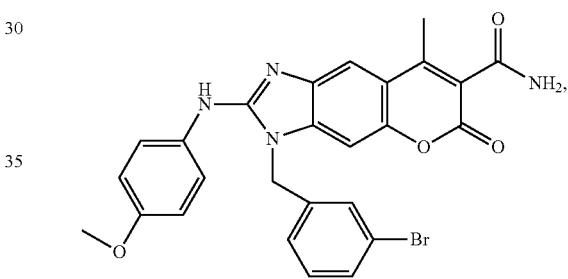
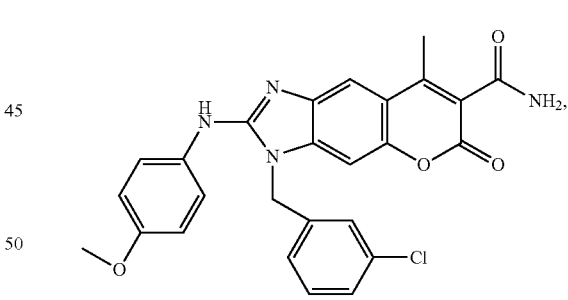
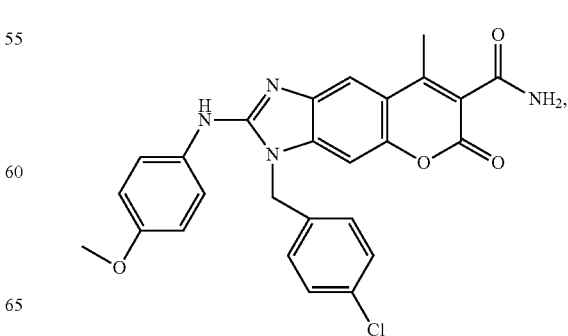

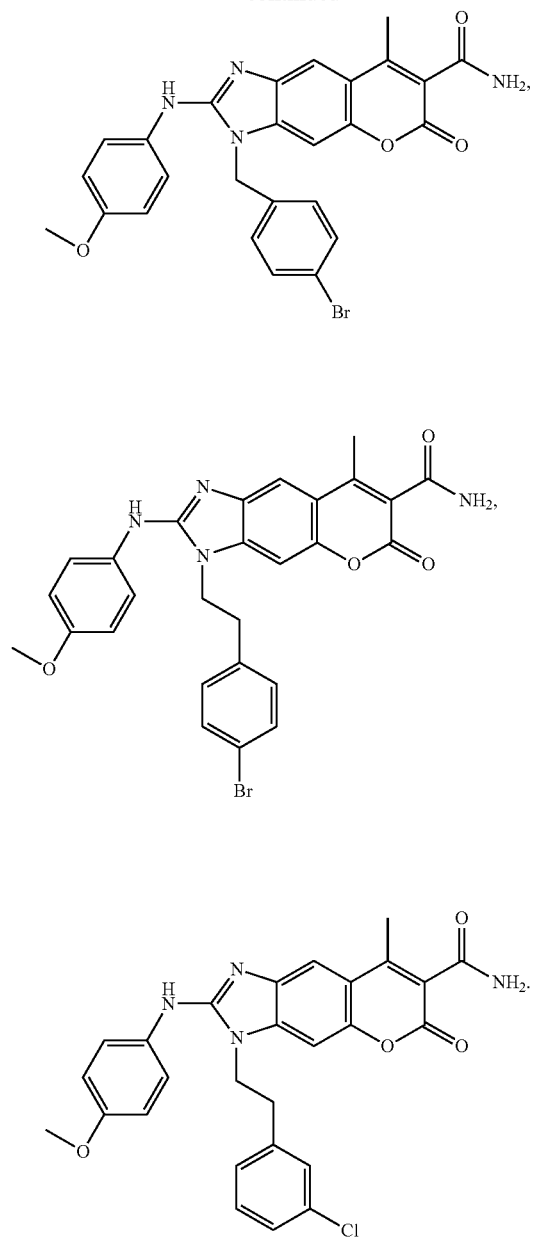

In other embodiments, the compound is:

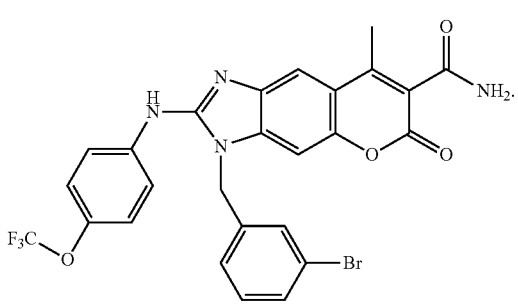

In still other embodiments, the compound is selected from the group consisting of:

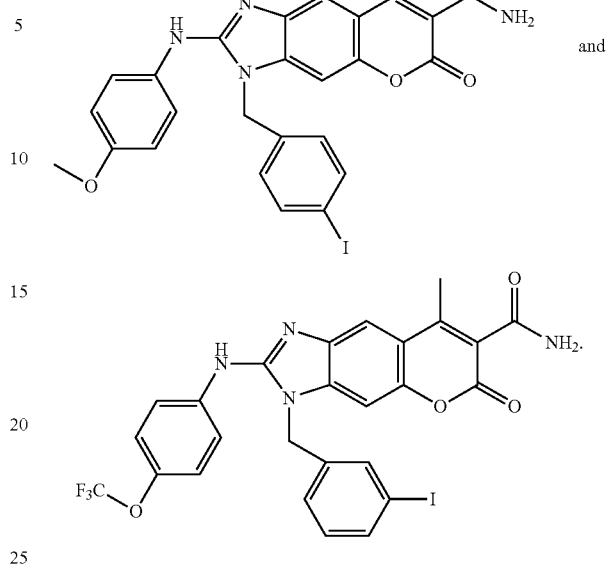

There is the proviso that compounds of Formula I of the present invention do not include the compound structures set forth below in Table A.

TABLE A 1. 3-Butyl-8-methyl-6-oxo-2-phenylamino-3,6-dihydro-chromeno[6,7-d]imidazole-7-carboxylic acid amide
2. 2-(2,6-Dimethyl-phenylamino)-8-methyl-6-oxo-3-propyl-3,6-dihydro-chromeno[6,7-d]imidazole-7-carboxylic acid amide
3. 3-sec-Butyl-2-(4-fluoro-phenylamino)-8-methyl-6-oxo-3,6-dihydro-chromeno[6,7-d]imidazole-7-carboxylic acid amide
4. 2-(4-Chloro-phenylamino)-3-cyclopentyl-8-methyl-6-oxo-3,6-dihydro-chromeno[6,7-d]imidazole-7-carboxylic acid amide
5. 2-(4-Bromo-phenylamino)-3-cyclohexyl-8-methyl-6-oxo-3,6-dihydro-chromeno[6,7-d]imidazole-7-carboxylic acid amide
6. 3-Benzyl-2-(4-methoxy-phenylamino)-8-methyl-6-oxo-3,6-dihydro-chromeno[6,7-d]imidazole-7-carboxylic acid amide
7. 3-[2-(4-Chloro-phenyl)-ethyl]-2-(3-methoxy-phenylamino)-8-methyl-6-oxo-3,6-dihydro-chromeno[6,7-d]imidazole-7-carboxylic acid amide
8. 8-Methyl-2-(3-nitro-phenylamino)-6-oxo-3-(2-pyrrolidin-1-yl-ethyl)-3,6-dihydro-chromeno[6,7-d]imidazole-7-carboxylic acid amide
9. 3-(3-Ethoxy-propyl)-8-methyl-2-(4-nitro-phenylamino)-6-oxo-3,6-dihydro-chromeno[6,7-d]imidazole-7-carboxylic acid amide
10. 8-Methyl-3-(2-morpholin-4-yl-ethyl)-2-(naphthalen-1-ylamino)-6-oxo-3,6-dihydro-chromeno[6,7-d]imidazole-7-carboxylic acid amide
11. 3-(2,4-Dimethoxy-benzyl)-2-(4-iodo-phenylamino)-8-methyl-6-oxo-3,6-dihydro-chromeno[6,7-d]imidazole-7-carboxylic acid amide
12. 2-(3-Bromo-phenylamino)-8-methyl-6-oxo-3-(2-phenoxy-ethyl)-3,6-dihydro-chromeno[6,7-d]imidazole-7-carboxylic acid amide
13. 2-(3-Chloro-phenylamino)-8-methyl-6-oxo-3-pyridin-2-ylmethyl-3,6-dihydro-chromeno[6,7-d]imidazole-7-carboxylic acid amide
14. 2-(3-Fluoro-phenylamino)-3-(3-imidazol-1-yl-propyl)-8-methyl-6-oxo-3,6-dihydro-chromeno[6,7-d]imidazole-7-carboxylic acid amide
15. 2-(2-Fluoro-phenylamino)-8-methyl-6-oxo-3-(tetrahydro-furan-2-ylmethyl)-3,6-dihydro-chromeno[6,7-d]imidazole-7-carboxylic acid amide
16. 2-(2-Chloro-phenylamino)-8-methyl-3-[2-(1-methyl-pyrrolidin-2-yl)-ethyl]-6-oxo-3,6-dihydro-chromeno[6,7-d]imidazole-7-carboxylic acid amide
17. 2-(3,5-Dichloro-phenylamino)-3-[2-(4-methoxy-phenyl)-ethyl]-8-methyl-6-oxo-3,6-dihydro-chromeno[6,7-d]imidazole-7-carboxylic acid amide
18. 2-(3,4-Dichloro-phenylamino)-8-methyl-6-oxo-3-[3-(2-oxo-pyrrolidin-1-yl)-propyl]-3,6-dihydro-chromeno[6,7-d]imidazole-7-carboxylic acid amide
19. 2-(2,4-Dichloro-phenylamino)-8-methyl-6-oxo-3-(2-piperidin-1-yl-ethyl)-3,6-dihydro-chromeno[6,7-d]imidazole-7-carboxylic acid amide In another embodiment, compounds of the invention of Formula I are selected from those set forth in Table B.

TABLE B 1. 2-(4-Bromo-phenylamino)-8-methyl-6-oxo-3-(2-phenoxy-ethyl)-3,6-dihydro-chromeno[6,7-d]imidazole-7-carboxylic acid amide
2. 2-(4-Methoxy-phenylamino)-8-methyl-6-oxo-3-(2-phenoxy-ethyl)-3,6-dihydro-chromeno[6,7-d]imidazole-7-carboxylic acid amide
3. 2-(3-Iodo-phenylamino)-8-methyl-6-oxo-3-(2-phenoxy-ethyl)-3,6-dihydro-chromeno[6,7-d]imidazole-7-carboxylic acid amide
4. 2-(4-Iodo-phenylamino)-8-methyl-6-oxo-3-(2-phenoxy-ethyl)-3,6-dihydro-chromeno[6,7-d]imidazole-7-carboxylic acid amide
5. 2-(2-Bromo-phenylamino)-8-methyl-6-oxo-3-(2-phenoxy-ethyl)-3,6-dihydro-chromeno[6,7-d]imidazole-7-carboxylic acid amide In another embodiment, compounds of the invention of Formula I are selected from those set forth in Table C.

TABLE C 1. 2-(3-Iodo-phenylamino)-8-methyl-6-oxo-3-prop-2-ynyl-3,6-dihydro-chromeno[6,7-d]imidazole-7-carboxylic acid amide
2. 3-(2-Hydroxy-ethyl)-2-(3-iodo-phenylamino)-8-methyl-6-oxo-3,6-dihydro-chromeno[6,7-d]imidazole-7-carboxylic acid amide
3. 2-(3-Iodo-phenylamino)-3-(2-methoxy-ethyl)-8-methyl-6-oxo-3,6-dihydro-chromeno[6,7-d]imidazole-7-carboxylic acid amide
4. 2-(3-Iodo-phenylamino)-3-[2-(4-methoxy-phenyl)-ethyl]-8-methyl-6-oxo-3,6-dihydro-chromeno[6,7-d]imidazole-7-carboxylic acid amide
5. 3-[2-(4-Bromo-phenyl)-ethyl]-2-(3-iodo-phenylamino)-8-methyl-6-oxo-3,6-dihydro-chromeno[6,7-d]imidazole-7-carboxylic acid amide
6. 2-(3-Iodo-phenylamino)-3,8-dimethyl-6-oxo-3,6-dihydro-chromeno[6,7-d]imidazole-7-carboxylic acid amide
7. 2-(3-Iodo-phenylamino)-8-methyl-6-oxo-3-propyl-3,6-dihydro-chromeno[6,7-d]imidazole-7-carboxylic acid amide
8. 3-Cyclopropylmethyl-2-(3-iodo-phenylamino)-8-methyl-6-oxo-3,6-dihydro-chromeno[6,7-d]imidazole-7-carboxylic acid amide
9. 3-(2,2-Difluoro-ethyl)-2-(3-iodo-phenylamino)-8-methyl-6-oxo-3,6-dihydro-chromeno[6,7-d]imidazole-7-carboxylic acid amide
10. 3-(3-Iodo-benzyl)-2-(3-iodo-phenylamino)-8-methyl-6-oxo-3,6-dihydro-chromeno[6,7-d]imidazole-7-carboxylic acid amide
11. 3-(3-Iodo-benzyl)-2-(4-methoxy-phenylamino)-8-methyl-6-oxo-3,6-dihydro-chromeno[6,7-d]imidazole-7-carboxylic acid amide
12. 3-(3-iodobenzyl)-2-(3-methoxyphenylamino)-8-methyl-6-oxo-3,6-dihydrochromeno[7,6-d]imidazole-7-carboxylic acid amide
13. 3-(3-iodobenzyl)-8-methyl-2-(3-(methylthio)phenylamino)-6-oxo-3,6-dihydrochromeno[7,6-d]imidazole-7-carboxylic acid amide
14. 2-(2,4-dimethoxyphenylamino)-3-(3-iodobenzyl)-8-methyl-6-oxo-3,6-dihydrochromeno[7,6-d]imidazole-7-carboxylic acid amide
15. 3-(3-bromobenzyl)-2-(4-methoxyphenylamino)-8-methyl-6-oxo-3,6-dihydrochromeno[7,6-d]imidazole-7-carboxylic acid amide
16. 3-(3-fluorobenzyl)-2-(4-methoxyphenylamino)-8-methyl-6-oxo-3,6-dihydrochromeno[7,6-d]imidazole-7-carboxylic acid amide
17. 3-(3-chlorobenzyl)-2-(4-methoxyphenylamino)-8-methyl-6-oxo-3,6-dihydrochromeno[7,6-d]imidazole-7-carboxylic acid amide
18. 3-(4-chlorobenzyl)-2-(4-methoxyphenylamino)-8-methyl-6-oxo-3,6-dihydrochromeno[7,6-d]imidazole-7-carboxylic acid amide
19. 3-(4-bromobenzyl)-2-(4-methoxyphenylamino)-8-methyl-6-oxo-3,6-dihydrochromeno[7,6-d]imidazole-7-carboxylic acid amide
20. 3-(4-iodobenzyl)-2-(4-methoxyphenylamino)-8-methyl-6-oxo-3,6-dihydrochromeno[7,6-d]imidazole-7-carboxylic acid amide
21. 3-(4-bromophenethyl)-2-(4-methoxyphenylamino)-8-methyl-6-oxo-3,6-dihydrochromeno[7,6-d]imidazole-7-carboxylic acid amide
22. 3-(3-chlorophenethyl)-2-(4-methoxyphenylamino)-8-methyl-6-oxo-3,6-dihydrochromeno[7,6-d]imidazole-7-carboxylic acid amide
23. 3-(3-chlorobenzyl)-8-methyl-6-oxo-2-(4-(trifluoromethoxy)phenylamino)-3,6-dihydrochromeno[7,6-d]imidazole-7-carboxylic acid amide
24. 3-(3-bromobenzyl)-8-methyl-6-oxo-2-(4-(trifluoromethoxy)phenylamino)-3,6-dihydrochromeno[7,6-d]imidazole-7-carboxylic acid amide
25. 3-(3-iodobenzyl)-8-methyl-6-oxo-2-(4-(trifluoromethoxy)phenylamino)-3,6-dihydrochromeno[7,6-d]imidazole-7-carboxylic acid amide
26. 3-(4-chlorobenzyl)-8-methyl-6-oxo-2-(4-(trifluoromethoxy)phenylamino)-3,6-dihydrochromeno[7,6-d]imidazole-7-carboxylic acid amide TABLE C-continued 27. 3-(4-bromobenzyl)-8-methyl-6-oxo-2-(4-(trifluoromethoxy)phenylamino)-3,6-dihydrochromeno[7,6-d]imidazole-7-carboxylic acid amide
28. 3-(3-bromophenyl)-2-(4-methoxyphenylamino)-8-methyl-6-oxo-3,6-dihydrochromeno[7,6-d]imidazole-7-carboxylic acid amide
29. 3-(4-bromobenzyl)-2-(4-cyanophenylamino)-8-methyl-6-oxo-3,6-dihydrochromeno[7,6-d]imidazole-7-carboxylic acid amide
30. 2-(4-cyanophenylamino)-3-(4-iodobenzyl)-8-methyl-6-oxo-3,6-dihydrochromeno[7,6-d]imidazole-7-carboxylic acid amide In another aspect, the present invention provides for labeled compounds of Formula I, wherein the structure of Formula I is as described above. As used herein, the term "labeled" refers to compounds of Formula I that contain unnatural proportions of atomic isotopes at one or more of the atoms that constitute such compound of Formula I. A labeled compound of Formula I can comprise unnatural amounts of a stable or unstable isotope. A "stable isotope" is any of two or more forms of an element in which the nuclei contains the same number of protons and electrons, but a different number of neutrons. Stable isotopes remain unchanged indefinitely (e.g., $^{19}$F or $^{13}$C), but "unstable" isotopes, however, are for example, radioactive isotopes that undergo spontaneous disintegration. In one embodiment, labeled compounds of the invention comprise unnatural proportions of unstable isotope (e.g., radioactive isotopes).

In one embodiment, the labeled compounds of Formula I can be labeled with stable isotopes, such as, $^{19}$F or $^{13}$C for MRS/MRI (Magnetic Resonance Spectroscopy/Magnetic Resonance Imaging) by general organic chemistry techniques known to the art. See, e.g., March, *J. ADVANCED ORGANIC CHEMISTRY: REACTIONS, MECHANISMS, AND STRUCTURE* (3rd Edition, 1985), the contents of which are hereby incorporated by reference.

In another embodiment, labeled compounds of Formula I are labeled with unstable isotopes and are radioactive. As used herein, the term "radioactive" refers to compounds of Formula I that contain unnatural proportions of an unstable radioactive isotope at one or more of the atoms that constitute such compound of Formula I; or in the alternative, the term "radioactive" refers to compounds of Formula I that further comprise a radioactive metal component, such as for example, $^{99m}$Tc.

In a preferred embodiment, radioactive compounds of the invention are labeled with radioactive isotopes selected from the group consisting of fluorine-18 ($^{18}$F), oxygen-15 ($^{15}$O), carbon-11 ($^{11}$C), Nitrogen-13 ($^{13}$N), iodine-125 ($^{125}$I), iodine-123 ($^{123}$I), iodine-124 ($^{124}$I), iodine-131 ($^{131}$I), bromine-75 ($^{75}$Br), and bromine-76 ($^{76}$Br). In a preferred embodiment, radioactive compounds of the invention are labeled with radioactive isotopes selected from the group consisting of fluorine-18 ($^{18}$F), oxygen-15 ($^{15}$O), carbon-11 ($^{11}$C), Nitrogen-13 ($^{13}$N) or iodine-125 ($^{123}$I). In another embodiment, radioactive compounds of the invention are labeled with radioactive isotopes selected from the group consisting of fluorine-18 ($^{18}$F), oxygen-15 ($^{15}$O) and carbon-11 ($^{11}$C). In another embodiment, radioactive compounds of the invention are labeled with radioactive isotopes selected from the group consisting of fluorine-18 ($^{18}$F) and carbon-11 ($^{11}$C). In another embodiment, radioactive compounds of the invention are labeled with radioactive isotopes selected from the group consisting of fluorine-18 ($^{18}$F). In another embodiment, radioactive compounds of the invention are labeled with iodine-125 ($^{125}$I). In another embodiment, radioactive compounds of the invention are labeled with iodine-124 ($^{124}$I).

The labeled compounds of Formula I can be labeled with radioactive isotopes by techniques well known in the art and are described, for example, by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986) the contents of which are hereby incorporated by reference. In one instance, the compounds of Formula I can be labeled with $^{123}$I as describe in, for example, Kulkarni, Int. J. Rad. Appl. & Inst. (Part B) 18: 647 (1991), the contents of which are hereby incorporated by reference. In addition, compounds of Formula I can be labeled with any suitable radioactive iodine isotope, such as, but not limited to, $^{131}$I, $^{125}$I, or $^{123}$I, by iodination of a diazotized amino derivative directly via a diazonium iodide, see Greenbaum, F. Am. J. Pharm. 108: 17 (1936); or by conversion of the unstable diazotized amine to the stable triazene; or by conversion of a non-radioactive halogenated precursor to a stable tri-alkyl tin derivative which then can be converted to the iodo compound by several methods well known to the art. See, Satyamurthy and Barrio J. Org. Chem. 48: 4394 (1983), Goodman et al., J. Org. Chem. 49: 2322 (1984), and Mathis et al., J. Labell. Comp. and Radiopharm. 1994: 905; Chumpradit et al., J. Med. Chem. 34: 877 (1991); Zhuang et al., J. Med. Chem. 37: 1406 (1994); Chumpradit et al., J. Med. Chem. 37: 4245 (1994). For example, a stable triazene or tri-alkyl tin derivative of a compound of Formula I is reacted with a halogenating agent containing $^{131}$I, $^{125}$I, $^{123}$I, $^{76}$Br, $^{75}$Br, $^{18}$F or $^{19}$F. Thus, the stable tri-alkyl tin derivatives of compounds of Formula I are novel precursors useful for the synthesis of many of the radioactively labeled compounds within the present invention.

The labeled compounds of Formula I can be labeled with known metal radiolabels, such as Technetium-99m ($^{99m}$Tc). Modification of the substituents to introduce ligands that bind such metal ions can be effected without undue experimentation by one of ordinary skill in the radiolabeling art. The metal radiolabeled compounds of Formula I can then be used to detect Aβ peptide aggregate deposits. Preparing radiolabeled compounds comprising $^{99m}$Tc is well known in the art. See, for example, Zhuang et al., "Neutral and stereospecific Tc-99m complexes: [99 mTc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Horn et al., "Technetium-99m-labeled receptor-specific small-molecule radiopharmaceuticals: recent developments and encouraging results" Nuclear Medicine & Biology 24(6):485-98, (1997).

The labeled compounds (e.g., radioactive compounds) of the invention are of Formula I, and within certain separate embodiments, encompass independently each of the subgenus of compounds described for compounds of Formula I as set forth above.

In one embodiment, radioactive compounds of the invention are those selected from Table A, Table B, or Table C.

Synthesis of Compounds:

The compounds of the invention can be prepared by synthetic methods generally known in art through solution phase or solid phase chemistry. For example, as shown in Scheme 1 below, using solid phase synthesis techniques, compounds and radioactive derivatives of Formula I can be prepared as follows. Deprotected Rink resin is coupled to coumarin derivative i using standard amino acid coupling chemistry. The leaving group X in the coupled product ii is displaced with an amine containing molecule to form the aryl amine product iii. The product iii, which contains a nitro group, can be reduced to provide iv which comprises a second aryl amino group. Compound v of Formula I can be formed upon reaction of iv with an aryl thiocyanate and cyclization of the resultant thiourea product and hydrolysis from the resin linker to provide compounds of the invention having Formula I. In Scheme 1, R can be hydrogen, hydrogen, alkyl, heteroalkyl, or haloalkyl group; R' is a non-hydrogen substituent; X is a leaving group, e.g., halogen, etc; and Ar is an aryl or heteroaryl group.

Further modifications of the above described method are known to one skilled in the art and are within the scope for use in the present invention. For example, compound of Formula I can be prepared as describe by Song et al. Tetrahedron (2004) 60:8605-8612, which is incorporated herein by reference.

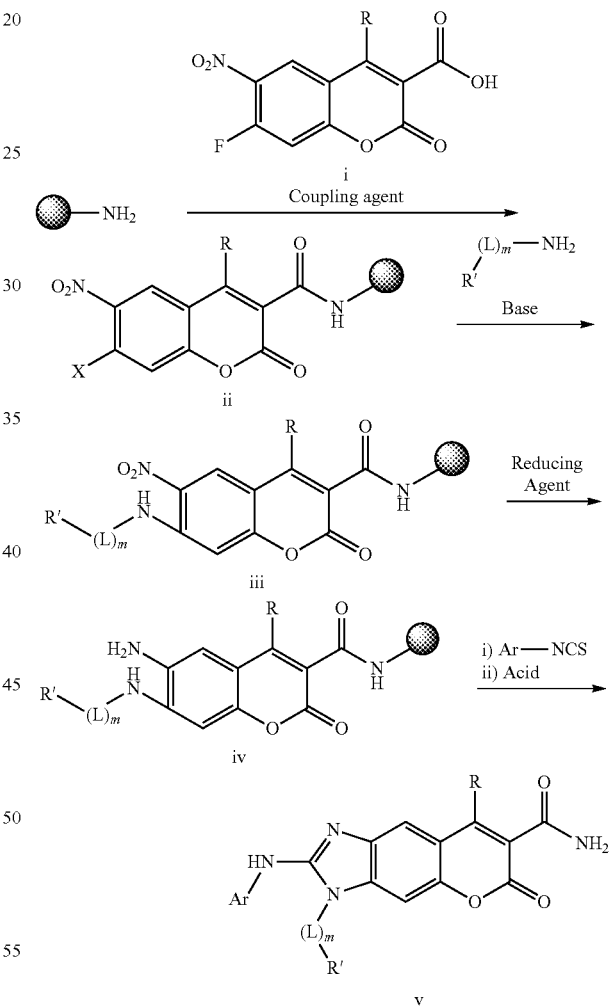

III. Pharmaceutical Compositions

In another aspect, the present invention relates to pharmaceutical compositions comprising a compound or labeled compound of Formula I and a pharmaceutically acceptable carrier or diluent. In one embodiment, pharmaceutical compositions comprise compounds of Formula 1 that do not embrace the compound structures set forth below in Table A. In another embodiment, pharmaceutical compositions of the invention comprise labeled compounds of Formula I. In one embodiment, a labeled compound is a radioactive compound of Formula I.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active ingredient is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

Other pharmaceutically acceptable carriers suitable for pharmaceutical compositions of the invention include aqueous solutions, non-toxic excipients, including salts, preservatives, buffers and the like, as described, for instance, in *REMINGTON'S PHARMACEUTICAL SCIENCES,* 15th Ed., Easton: Mack Publishing Co., pp. 1405-1412 and 1461-1487 (1975) and *THE NATIONAL FORMULARY XIV,* 14th Ed. Washington: American Pharmaceutical Association (1975), and the *UNITED STATES PHARMACOPEIA XVIII.* 18th Ed. Washington: American Pharmaceutical Association. (1995), the contents of which are hereby incorporated by reference.

In one embodiment, the present invention provides for an injectable pharmaceutical composition comprising a compound or labeled compound of Formula I, the composition further comprising serum albumin and a phosphate buffer containing NaCl. The injectable pharmaceutical composition can comprise about 10 mg of human serum albumin and from about 0.5 to 500 micrograms of a compound or labeled compound of Formula I per milliliter of phosphate buffer containing NaCl.

The pharmaceutical compositions of the invention comprise compounds or labeled compounds of Formula I, and within certain separate embodiments, can comprise independently each of the subgenus of compounds described for compounds of Formula I as set forth above.

IV. Methods of Use

As demonstrated by in vitro and in vivo tests discussed in detail below, in one embodiment of the invention, compounds or labeled compounds of Formula I are effective at binding to Aβ peptide aggregates (e.g., AβO). In another embodiment of the invention, compounds or labeled compounds of Formula I can reduce the size or prevent the growth of Aβ peptide aggregates (e.g., AβO) in a patient. In another embodiment, compounds or labeled compounds of Formula I are effective to prevent the binding of Aβ peptide aggregates to synapses in a patient.

The data presented herein also demonstrate that compounds or labeled compounds of Formula I, e.g., Compound A, can rapidly pass though the BBB and have little short term toxicity. Therefore, in another embodiment, the present invention provides for compounds or labeled compounds of Formula I for the treatment of diseases caused by Aβ peptide aggregation or deposition, e.g., Alzheimer's disease, in a patient.

In addition, compounds or labeled compounds of Formula I bind to and are retained by Aβ peptide aggregates deposits (e.g., plaques) with a high degree of specificity. Furthermore, compounds or labeled compounds of Formula I are fluorescent, and can also can be labeled with stable and unstable isotopes. As such, compounds or labeled compounds of Formula I can be useful as a biomedical probes. In one embodiment, compounds or labeled compounds of Formula I are useful as biomedical probes for in vivo or in vitro imaging of Aβ peptide aggregates. In another embodiment, radioactive compounds of Formula I are useful as biomedical probes for in vivo or in vitro imaging of Aβ peptide aggregates. In another embodiment, radioactive compounds of Formula I are useful for in vivo imaging of Aβ peptide aggregate depositions (e.g., plaques) in a patient suffering from Alzheimer's or other conditions of amyloidosis.

In view of the above, the present invention provides for a method of detecting the presence of Aβ peptide aggregates in a patient comprising: (i) administering to a patient a detectable quantity of a compound of Formula I, wherein the compound of Formula I binds to Aβ peptide aggregates; and (ii) imaging the patient to detect the presence of the compound of Formula I, thereby detecting the presence of Aβ peptide aggregates in the patient. Also, the present invention provides for a method of detecting the presence of Aβ peptide aggregates in a patient comprising: (i) administering to a patient a detectable quantity of a labeled compound of Formula I, wherein the labeled compound of Formula I binds to Aβ peptide aggregates; and (ii) imaging the patient to detect the presence of the compound of Formula I, thereby detecting the presence of Aβ peptide aggregates in the patient. Within one aspect of this embodiment, the method of detecting the presence of Aβ peptide aggregates in a patient comprises administering a radioactive compound of Formula I. In one embodiment, the detection of Aβ peptide aggregates in a patient is accomplished using Positron Emission Tomography (PET) or Single Photon Emission Computed Tomography (SPECT). As used herein, the term "detectable quantity" means an amount compound that is sufficient to enable the imaging of binding of the compound to Aβ peptide aggregates.

The methods of the invention utilize compounds or labeled compounds of Formula I, and within separate embodiments, the disclosed methods comprise the use of, independently, each of the subgenus of compounds described for compounds of Formula I as set forth above. In one embodiment, each of the disclosed methods utilize a compound selected from the group of compounds presented on Table A, Table B and Table C.

For the treatment of diseases or conditions caused by Aβ peptide aggregation (e.g., amyloidosis) and for imaging purposes, the compounds or labeled compounds of the present invention; or their pharmaceutical compositions, can be administered by oral, parenteral (e.g., intramuscular, intraperitoneal, intravenous, ICV, intracisternal injection or infusion, subcutaneous injection, by implantation, by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

A. Binding to Aβ Peptide Aggregates

Figure 2:
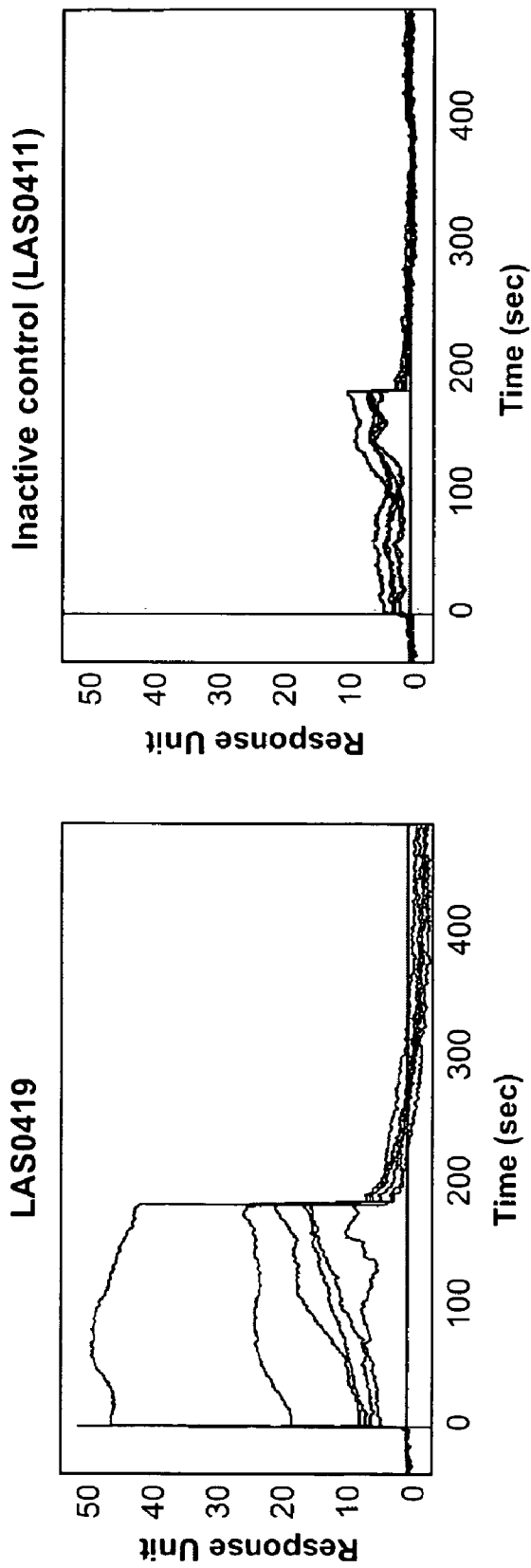
FIG. 2 provides the SPR data obtained for compounds of the invention. LAS0419 is Compound A and LAS0411 is Compound B of FIG. 1.

The compounds or labeled compounds of Formula I can bind to Aβ peptide aggregates. To detect the binding of compounds of Formula I to Aβ peptide aggregates, e.g., Aβ oligomers, the inventors developed a quantitative Surface Plasmon Resonance spectroscopy (SPR)-based method to measure the binding affinity of compound of Formula I to Aβ oligomers (see, FIG. 2) In this method, a commercially available streptavidin chip is first saturated with biotinylated AβO, which is prepared by mixing a 1:10 ratio of biotinylated and unbiotinylated $A\beta_{1\text{-}42}$ peptide. The binding of injected compound in the flow phase to immobilized AβO is measured by the response unit (RU) elicited. SPR data was obtained for Compound A and Compound B, at a series of concentrations ranging from 0.3 μM to 6.3 μM and from 1.25 μM to 40 μM, respectively (see, FIG. 2). One RU represents about 1 pg/mm$^2$ of the analytes on the surface matrix of the sensor chip. In FIG. 2, the left-hand panel contains the SPR data that shows that Compound A binds to AβO. It has been discovered that Compound A (see, FIG. 1 for structure) binds to immobilized AβO with comparable affinity as compared to another known amyloid binding ligand, "Pittsburgh Compound B" (PIB), (see, Klunk, et al., *Ann Neurol.* (2004) 55:306-319). The calculated binding affinity (KD) for Compound A is 530 nM. The calculated binding affinity (KD) of Thioflavin T (ThT) is 498 nM (see, Maezawa et al. *J. Neurochem.* published online Oct. 22, 2007, DOI: 10.1111/j.1471-4159.2007.04972.x.), which is incorporated herein by reference for all purposes. Using SPR spectroscopy, a non-binding compound, i.e., Compound B, was also identified (see, FIG. 2, right panel). As discussed in detail below, Compound B was found to be ineffective at protecting cells from Aβ peptide aggregate associated toxicity.

Figure 4A:
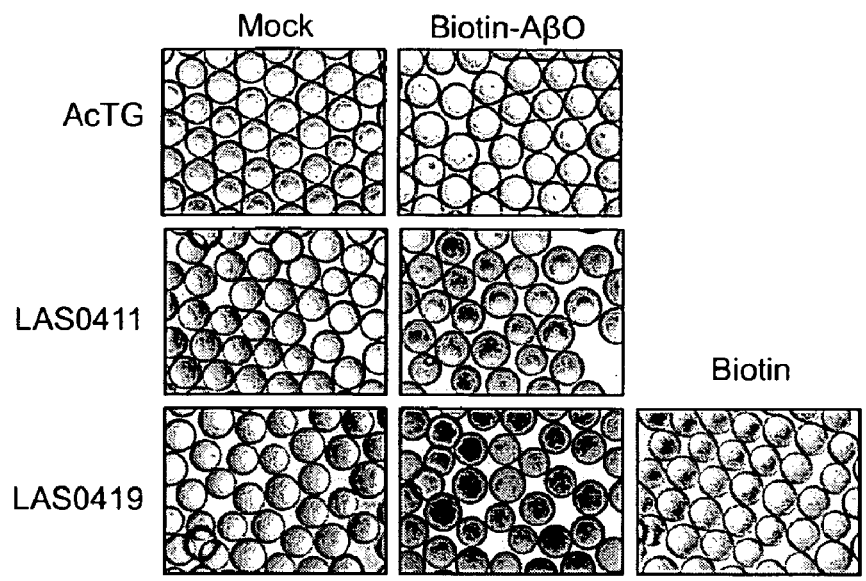
FIG. 4A and FIG. 4B relate to the on-bead binding assay results for compounds of the invention. LAS0419 is Compound A and LAS0411 is Compound B of FIG. 1.
Figure 4B:
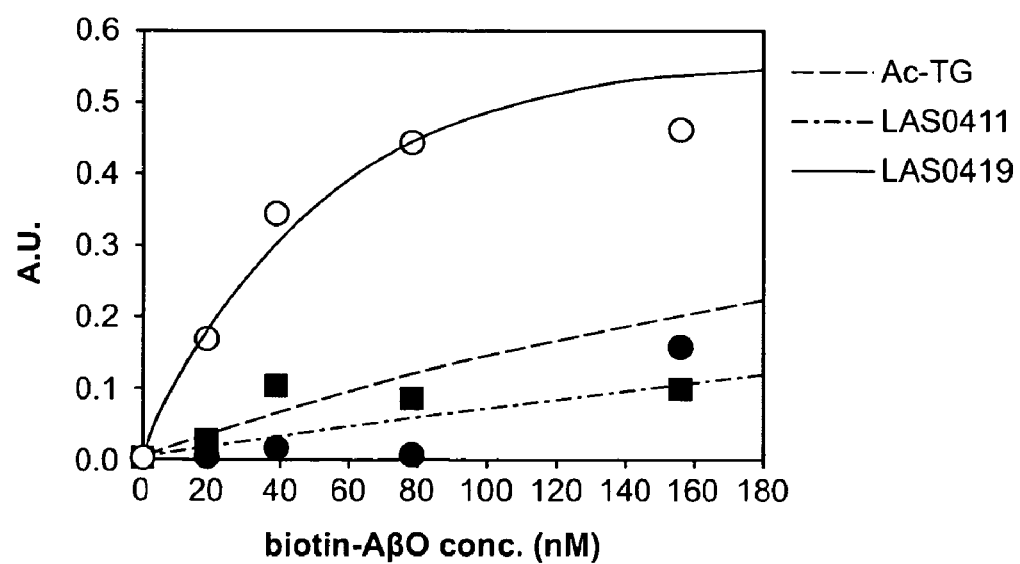

The binding affinity of Compounds A and B to Aβ peptide aggregates was also studied using an "On-Bead" binding assay. The test results presented in FIG. 4A and FIG. 4B clearly showed that Compound A, but not Compound B, binds to AβO. Compounds A and B were synthesized on TentaGel resin beads (Rapp Polymere GmbH, Tubingen, Germany) and tested for their binding to biotinylated AβO. Generally, the AβO bound to the beads were detected by streptavidin horseradish peroxidase (HRP), and subsequent color development was achieved using the soluble HRP substrate TMB (i.e., 3,3',5,5'-tetramethylbenzidine). The On-Bead binding assay was modified to be useful as a screening method. More particularly, in the assay, Ac-TG beads, Compound A beads, and Compound B beads were incubated with solvent (i.e., no AβO) or with biotinylated AβO (Biotin-AβO) for 1 hour at room temperature. As an additional control, Compound A beads were incubated with biotin only. AβO bound to the to the beads were detected by streptavidin alkaline phosphatase (AP) and the colorized using the substrate BCIP (i.e., 5-bromo-4-chloro-3-indolyl phosphate), which formed insoluble indigo precipitates on the beads (see, FIG. 4A). In a separate experiment, conducted as described above, except for the fact that streptavidin-HRP (horseradish peroxidase) was used to detect the bound AβO, which allowed for the quantification of subsequent color development by the soluble HRP substrate TMG. Compound A showed satiable binding to AbO (AU=arbitrary unit). The test results shown in FIG. 4A and FIG. 4B shows that the beads comprising Compound A, but not those comprising Compound B, bind to AβO. In addition, in the absence of AβO, the beads comprising Compound A did not show non-specific binding to biotin.

B. Depolymerizing Aβ Peptide Aggregates

Figure 3A:
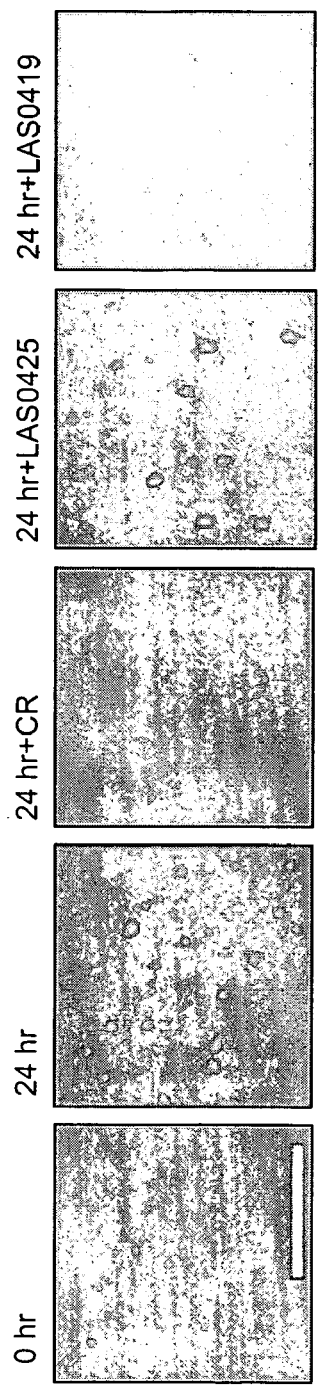
FIG. 3A, FIG. 3B and FIG. 3C relate to the Atomic Force Microscopy (AFM) data obtained for compounds of the invention. LAS0419 is Compound A and LAS0425 is Compound C of FIG. 1.
Figure 3C:
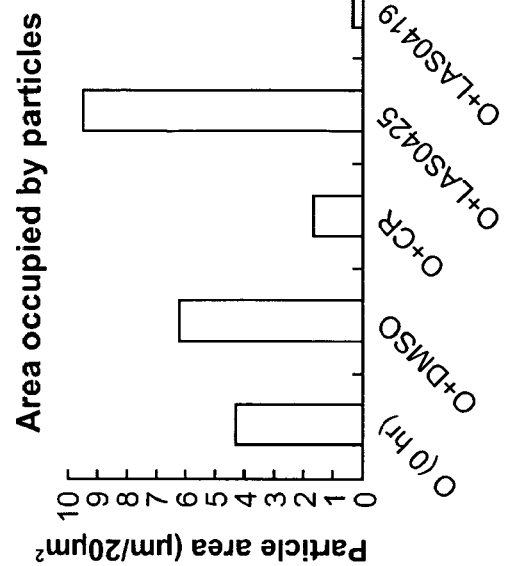
Figure 3B:
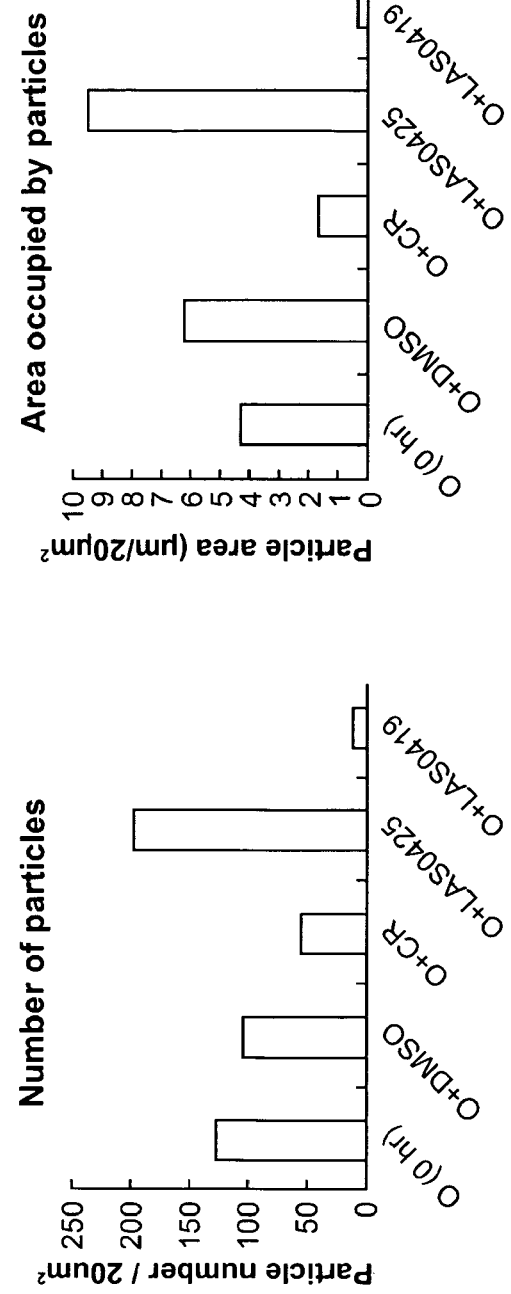

Atomic force microscopy (AFM) was used to evaluate the effectiveness of compounds of Formula I to depolymerize Aβ peptide aggregates, i.e., AβO (see, FIG. 3A, FIG. 3B, FIG. 3C). In this experiment, Congo Red (CR), a known anti-Aβ aggregation compound, was utilized as a positive control. The AFM experiment was performed as described in Maezawa, I. et al. (2006) *J. Neurochem.* 98:57-67; Hong H-S et al. *Brain Research* (2007) 1130:223-234. More specifically, for this experiment, AβO was incubated at 25° C. for 24 hours in the absence or presence of 10 equivalents of selected test compounds, i.e., Congo Red, Compounds A, and Compound B. AFM images were taken after a 24-hour incubation period (see, FIG. 3A). The analysis of the AFM images shows that Compound A (a representative compound of Formula I) appears able to depolymerize pre-formed AβO to smaller oligomer units or to monomers that were not detectable by AFM. The depolymerization effect of Compound A appears to be stronger than Congo Red. In contrast, Compound B showed no depolymerization effect. The average particle number and the area covered by particles per 20 μm$^2$ in the AFM images were quantified from ten randomly selected field by the Colony program (Fuji Photo, Japan) as and is shown in FIG. 3B and FIG. 3C, respectively.

Figure 5A:
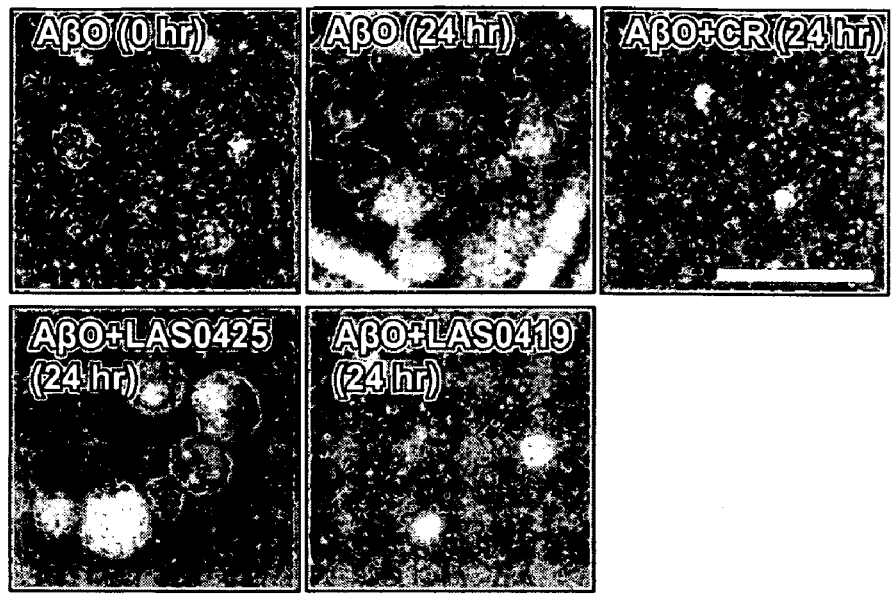
FIG. 5A and FIG. 5B relate to the Electron Microscopy (EM) data obtained for compounds of the invention. LAS0419 is Compound A and LAS0425 is Compound C of FIG. 1.
Figure 5B:
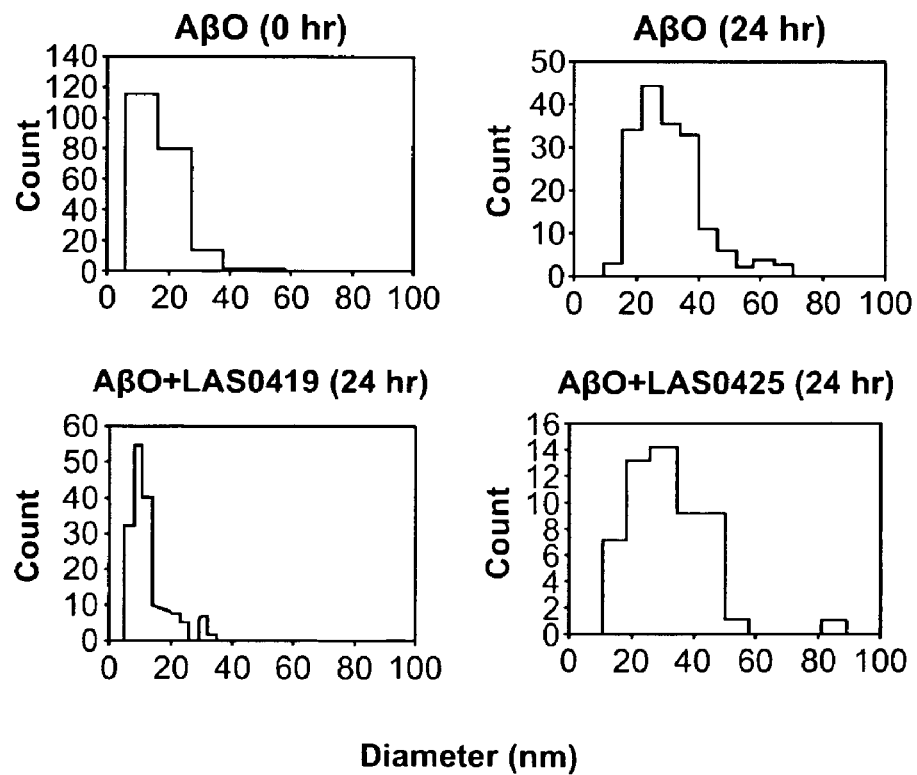

To address the possible alternative explanation that the depolymerization effect observed for Compound A in the AFM experiment is due to Compound A altered binding of AβO to the AFM mica, the effect of Compound A and Compound B and Congo Red on AβO size was further analyzed by electron microscopy (EM) (see FIG. 5A and FIG. 5B). The electron micrograph experiment was performed as described in Hong et al. *Brain Res.* (2007) 1130:223-234. The representative electron micrographs presented in FIG. 5A show the size of the AβO aggregates after incubation with either Compound A, Compound B or Congo Red. FIG. 5B contains a histogram, which illustrates the size distribution of AβO without treatment or with treatment with Compound A, Compound B or Congo Red. It is apparent from EM images in FIG. 5A and in the histograms shown in FIG. 5B that after 24 hour incubation at 25° C. and in the absence of treatment with Compound A or Congo Red, AβO grew in size. In contrast, incubation of AβO with Compound A or Congo Red resulted in the reduction in the number and size of AβO. Not surprisingly, Compound B which earlier tests showed does not bind to AβO, also did also did not stop the growth of AβO. The above experiment shows that compounds and labeled compounds of Formula I can reduce the size of Aβ peptide aggregates.

C. Reducing the Binding of Aβ Peptide Aggregates to Synapses

Compounds or labeled compounds of Formula I, e.g., Compound A, can reduce the binding of AβO to synapses. The strong binding of AβO to synapses induces aberration in synapse composition, shape, and density, and was proposed as the molecular basis for the loss of connectivity in AD (see, Lacor, et al., *J. Neurosci.* (2007) 27:796-807). A synaptic binding assay was performed as described by Lacor et al. (2007), which is incorporated herein by reference, with minor modifications to test the effectiveness of a compound of Formula I (e.g., Compound A) to reduce or to prevent the binding of AβO to synapses. The assay results are shown in FIG. 6. AβO prepared from the N-terminal biotinylated Aβ$_{1-42}$ peptide was incubated either with 10 equivalents compounds (i.e., 100 nM AβO: 1 μM Compound A), or with DMSO (i.e., the solvent for the compounds used only as a negative control) for five minutes, then added to cultured mouse hippocampal neurons that had been cultured 21 days in vitro. After 5 minute incubation, the neurons were washed, fixed, and stained with streptavidin-Alexa594 for bound AβO. A representative image of each assay condition is presented in FIG. 6. Analysis of the DMSO control culture, showed abundant fluorescent puncta within dendritic arbors, which were proven to be the post-synaptic sites. In the cultures containing either Congo Red (CR) or Compound A, a substantially reduced number of puncta was observed, which indicated that both CR and Compound A blocked the binding of AβO to synapses. The density of puncta per unit dendritic area was quantified using the Image J program and the resulting bar graph is presented in the far right panel. The synaptic binding assay results shown in FIG. 6 demonstrates that compounds of Formula I, such as, Compound A, have synapto-protective effects.

D. Preventing Cell Toxicity

Figure 7A:
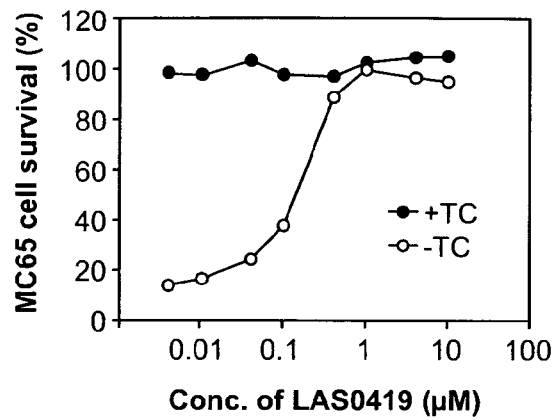
FIG. 7A and FIG. 7B relate to the MC65 cell proliferation assay data obtained for compounds of the invention. LAS0419 is Compound A of FIG. 1. LRL03 is (S)—N-(1-amino-3-(4-hydroxyphenyl)-1-oxopropan-2-yl)-2-(9-ethyl-9H-carbazol-3-yl)-1-(3-(2-oxopyrrolidin-1-yl)propyl)-1H-benzo[d]imidazole-5-carboxamide and LRL15 is 2-(2-bromophenylamino)-1-(2-phenoxyethyl)-1H-benzo[d]imidazole-5-carboxamide.
Figure 7B:
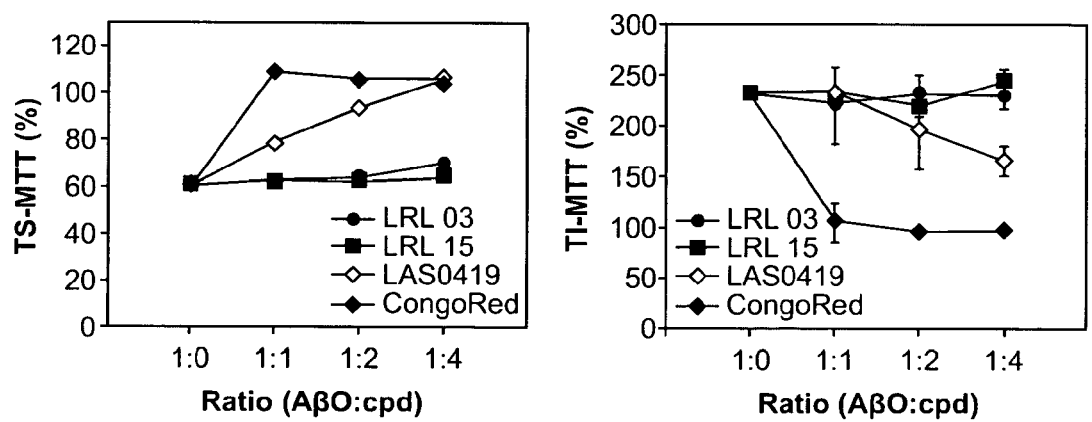

Surprisingly, it has been discovered that compounds or labeled compounds of Formula I, e.g., Compound A, are capable of protecting neuron-like cells from Aβ peptide aggregate toxicity, e.g., AβO toxicity, within both intracellular and extracellular sites. The MC65 cell protection assay and the rapid MTT-FE assay as described by Hong et al. *Brain Res.* (2007) 1130:223-234, which is incorporated herein by reference, were performed to demonstrate this effect. In the MC65 cell protection assay, cytotoxicity associated with intraneuronal AβO was induced by removal of the C99 transgene suppressor, tetracycline (TC). Compound A, at concentrations shown in FIG. 7A, was added at the same time as TC removal. After 72 hour incubation period, MC65 cell viability was assessed by conventional MTT assay and the results are shown FIG. 7A. The data presented in FIG. 7A are expressed as mean percent viability (n=2) with parallel positive TC cultures set for reference at 100%. The estimated $EC_{50}$ for Compound A is 187 nM. In the rapid MTT formazan exocytosis (MTT-FE) assay, AβO was combined with LRL 03, LRL 15, Compound A or Congo Red (2.5 μM solution) at a ratio of 1:0, 1:1, 1:2 or 1:4 (AβO:Compound) and incubated for 1 hour, followed by measurement of the degree of formazan exocytosis. The compounds LRL 03 and LRL 15 are related compounds having a benzimidazole core that are not within the scope of the present invention. In particular, cellular MTT formazan was fractionated into the Triton soluble (TS) and insoluble (TI) MTT and quantified and shown in FIG. 7B. (The data presented in FIG. 7B is expressed as mean percentages with mock treatment (i.e., DMSO solvent only) group set at 100% (n=3).) Notably, an observed decrease in TS-MTT and an increase in TI-MTT in a culture indicates cell toxicity. The cell viability assays demonstrate that Compound A and Congo Red are able to neutralize AβO cytotoxicity.

Figure 8A:
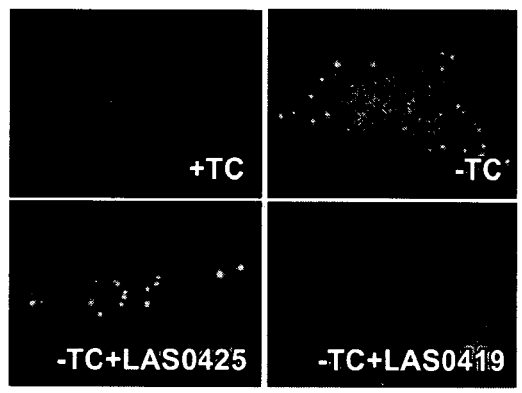
FIG. 8A and FIG. 8B relate to the immunocytochemical and Western blot data obtained for compounds of the invention. LAS0419 is Compound A and LAS0425 is Compound C of FIG. 1. LRL13 is (S)—N-(1-amino-3-(3,4-dihydroxyphenyl)-1-oxopropan-2-yl)-2-(3-bromophenylamino)-1-(2-phenoxyethyl)-1H-benzo[d]imidazole-5-carboxamide. LRL19 is 2-(4-iodophenylamino)-1-(2-phenoxyethyl)-1H-benzo[d]imidazole-5-carboxamide.

To determine if the cell protection effects observed for Compound A in the MC65 cell protection assay is attributed to its ability to prevent the formation of intracellular AβO, immunocytochemical and Western blot studies were performed. MC65 cells were cultured for 24 hours and then immunostained with oligomer specific antibody A11 (see, Kayed et al. *Biol Chem.* (2004) 279:46363-46366). As shown in FIG. 8A, intracellular AβO (red fluorescence) was seen in negative TC conditions (i.e., after the transgene (APP-C99) was activated), but not observed in positive TC conditions. Importantly, Compound A at 1 μM completely inhibited AβO formation. In contrast, Compound B at 1 μM, which did not prevent MC65 cell death, also did not inhibit AβO formation.

Figure 8B:
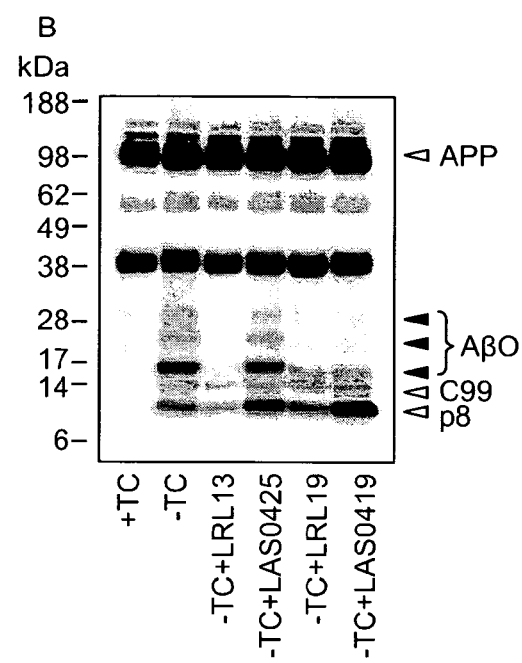

In FIG. 8B, MC65 cell homogenates from 24 hour cell cultures from the MC65 cell protection assay were analyzed by SDS-PAGE and Western blot using the 6E10 anti-Aβ antibody, which resulted in the identification of several bands representing SDS-stable AβO or fragments of AβO; or Aβ dimers (i.e., the P8 band). See, Maezawa et al. *J Neurochem* (2006) 98:57-67, which is incorporated herein by reference. Notably, compounds that protect MC65 cells from death, such as for example, Compound A, LRL 13 and LRL 19 at 1 μM, decreased the levels of SDS-stable AβO, but the inactive Compound B did not. Also, it appears that Compound A causes an increase in Aβ dimer formation. LRL 13 and LRL 19 are related compounds having a benzimidazole core that are not within the scope of the invention.

Provided below in Table D is the in vitro activity data of certain compounds of Formula I in when tested in the MC65 cell viability assay, as described above. In the activity column, the symbol + represents an $EC_{50}$>10 μM; the symbol ++ represents an EC50 value of between about 1 μM and about 10 μM; the symbol +++ represents and EC50 value of less than 1 μM.

TABLE D

| No. | Structure | $EC_{50}$ |
| --- | --- | --- |
| D.1 | 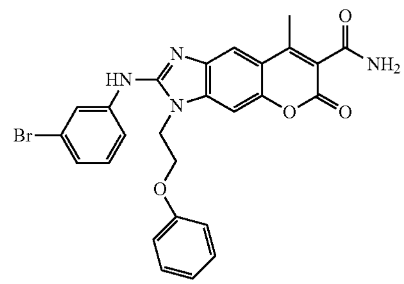 | +++ |
| D.2 | 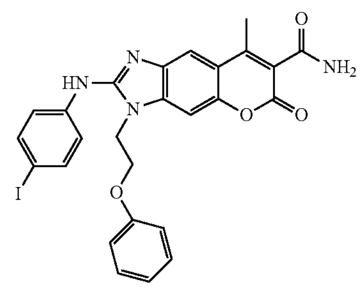 | +++ |
| D.3 | 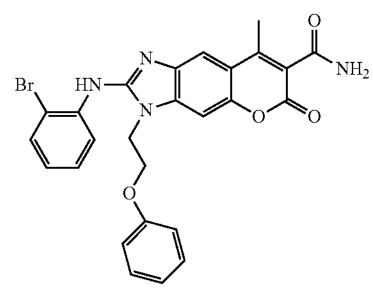 | + |
| D.4 | 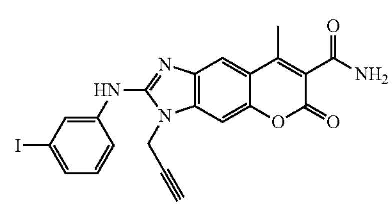 | ++ |
| D.5 | 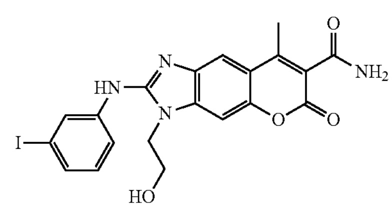 | + |
| D.6 | 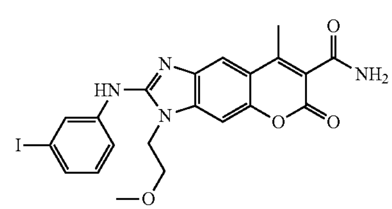 | + |

TABLE D-continued

| No. | Structure | EC$_{50}$ |
|---|---|---|
| D.7 | 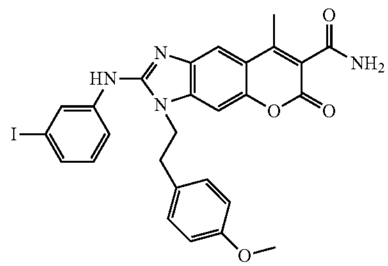 | +++ |
| D.8 | 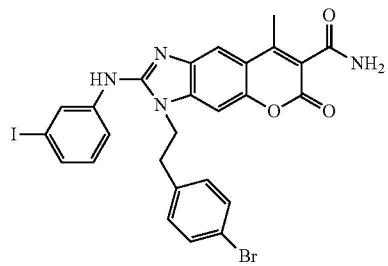 | +++ |
| D.9 | 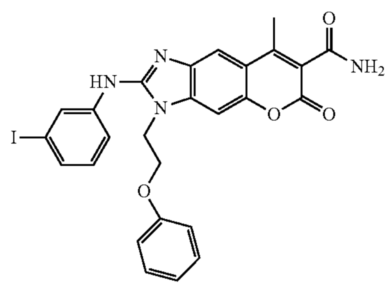 | +++ |
| D.10 | 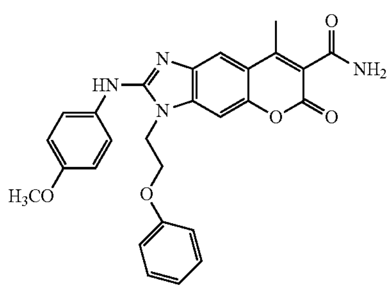 | +++ |
| D.11 | 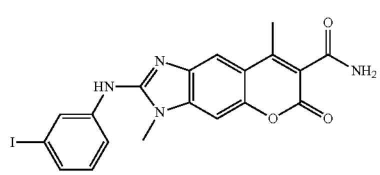 | ++ |
| D.12 | 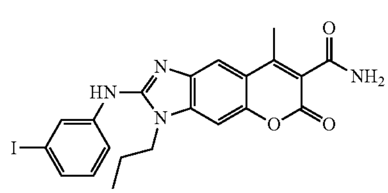 | +++ |
| D.13 | 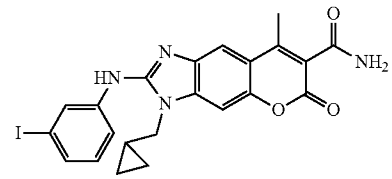 | +++ |
| D.14 | 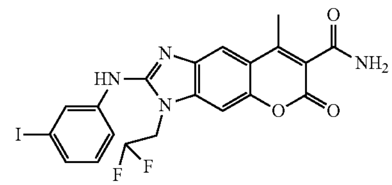 | ++ |
| D.15 | 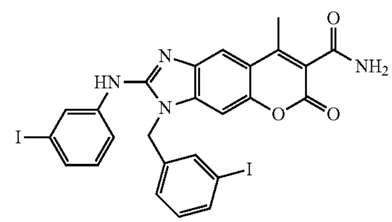 | +++ |
| D.16 | 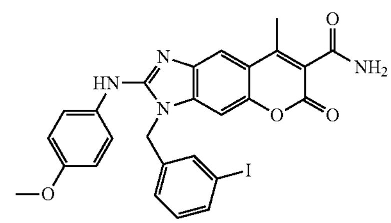 | +++ |
| D.17 | 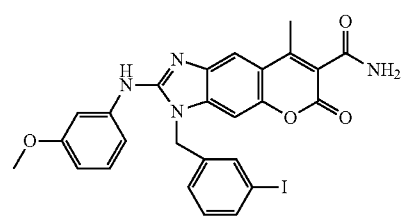 | +++ |
| D.18 | 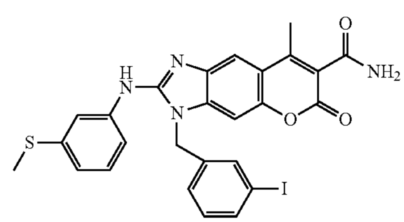 | +++ |
| D.19 | 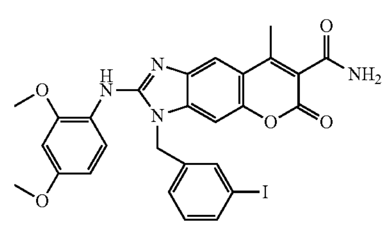 | +++ |

| No. | Structure | EC$_{50}$ |
|---|---|---|
| D.20 | 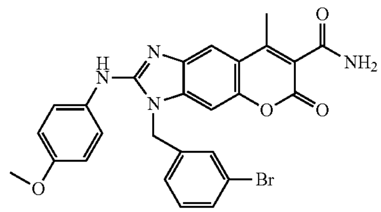 | +++ |
| D.21 | 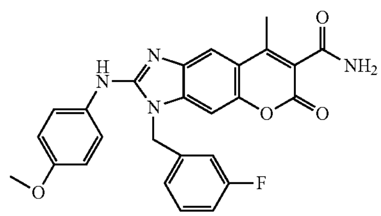 | +++ |
| D.22 | 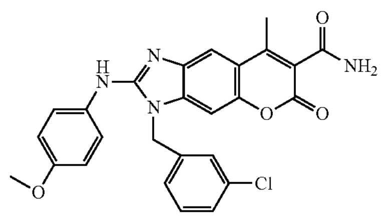 | +++ |
| D.23 | 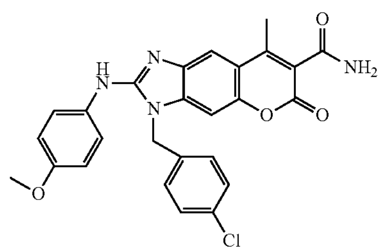 | +++ |
| D.24 | 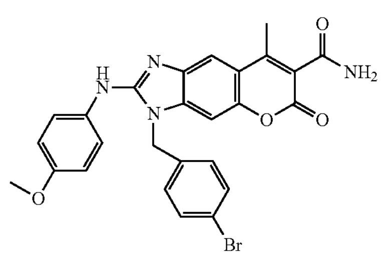 | +++ |
| D.25 | 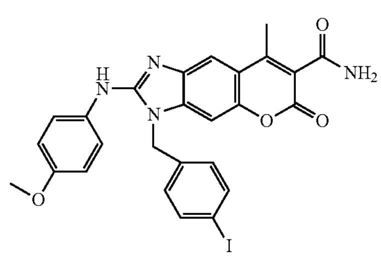 | +++ |
| D.26 | | +++ |
| D.27 | | +++ |
| D.28 | | +++ |
| D.29 | | +++ |
| D.30 | | +++ |
| D.31 | | +++ |

TABLE D-continued

| No. | Structure | EC$_{50}$ |
|---|---|---|
| D.32 | 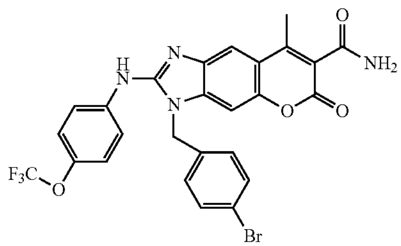 | +++ |
| D.33 | 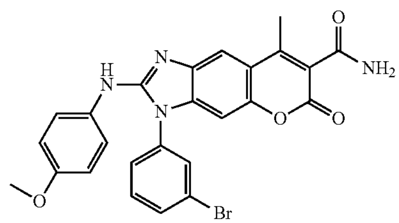 | + |
| D.34 | 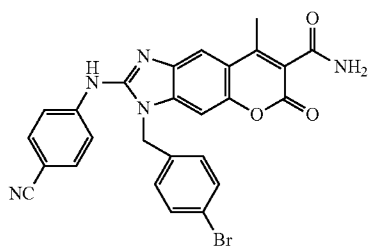 | +++ |
| D.35 | 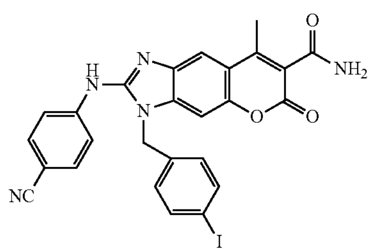 | +++ |

As disclosed above, Compound A has been identified as a potent compound for preventing the aggregation of Aβ peptides and for preventing cell death associated with AβO toxicity. In particular, the inventors noted that in the MC65 cell protection assay Compound A, which comprises a 3-bromophenyl, was significantly more potent than its isomeric compound, i.e., Compound C, which comprises a 2-bromo-phenyl ring. To explain the discrepancy in activity between these two isomers, the inventors performed computational docking of the 2-bromo (Compound C) and 3-bromo (Compound A) isomers with the model structures formed by two misfolded Aβ peptides originally reported by Petkova et al. *Proc Natl Acad Sci USA* (2002) 99:16742-16747. In this model, residues 12-24 and 30-40 adopt β-strand conformations and form parallel β-sheets through hydrophobic interaction and intermolecular hydrogen bonding. Residues 25-29 contain a bend in the peptide backbone that brings the two β-sheets in close contact through sidechain-sidechain interactions. The bend is stabilized by a salt bridge formed between Asp23 and Lys28.

Shown in FIG. 9A and FIG. 9B is the lowest energy conformation of Compound A and Compound C, respectively, each docked in the misfolded Aβ peptide structure as described above. In the docked structure of active Compound A (see, FIG. 9A), hydrogen bonds exists between (1) the amino group (NH$_2$) of Compound A with the amide carbonyl group (C=O) of Ile31 residue of Aβ (at a distance of 2.3 Å); (2) the phenyl ether oxygen atom of Compound A with the amide NH group of Met35 of Aβ (at a distance of 2.3 Å); and (3) the amino group (NH) (attached at C2 of the imidazole ring system) of Compound A with the side chain carboxylate ion of Asp23 of Aβ (at a distance of 3.2 Å). Notably, Asp23 is used in the salt bridge formation of Aβ, which leads to the β-turn (see, Petkova et al., *Proc Natl Acad Sci USA* (2002) 99:16742-16747). In contrast, the docked structure of inactive Compound C reveals no hydrogen bond formation between compound C and the Aβ-peptide (see, FIG. 9B). Thus, without being bound by any theory, it is possible to explain the discrepancy in the biological potency of Compounds A and C by the docking results, described above. Notably, the docking results suggest a possible disaggregation mechanism by which the aryl amine NH functional group of Compound A binds to Asp23 in the Aβ peptide and dissociates the salt bridge between Asp23 and Lys28 to result in the destabilization of the β-sheet structure of the Aβ peptide, to consequently prevents the formation of Aβ peptide aggregates (e.g., oligomers).

E. Binding to Aβ Fibrils

Figure 10:
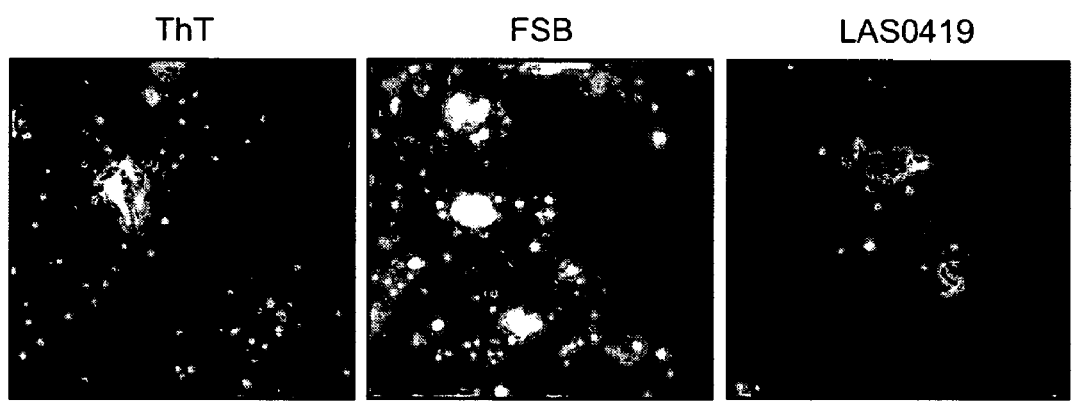
FIG. 10 relates to the Aβ fibrils binding assay data obtained for compounds of the invention. LAS0419 is Compound A of FIG. 1.
Figure 13:
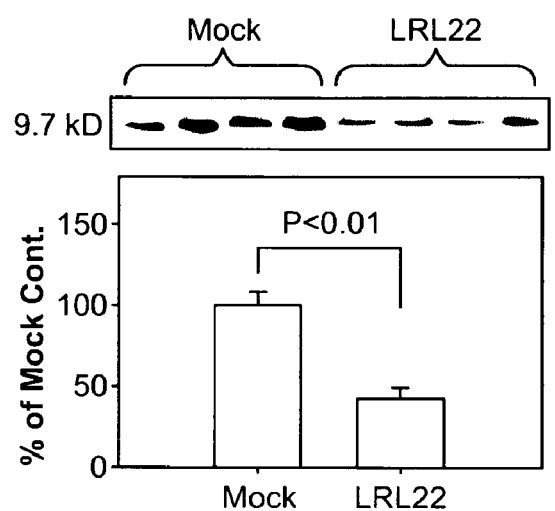
FIG. 13 shows compound A reduces the level of RIPA (Radioimmune precipitation assay buffer)-soluble Aβ dimer. Brain extractions used were from the same mice described in FIG. 12. Shown is the 9.7 kD dimer in the Western blot analyzed with the anti-Aβ3-8 antibody 6E10. Compound A significantly reduced the levels of the soluble, highly neurotoxic Aβ dimers in 5xFAD mice. LRL22 is Compound A of FIG. 1.

The ability of compounds or labeled compounds of Formula I, e.g., Compound A, to bind to Aβ fibrils was examined, in view of the possible shared binding sites between the fibrillar and oligomeric forms of Aβ peptide aggregates. In particular, compound A, which is a fluorescent compound, was used to stain Aβ fibrils formed in vitro by aggregation of Aβ$_{1-42}$ peptide. As shown in FIG. 10, Compound A clearly stained Aβ fibrils, although this compound was susceptible to photobleaching. For comparison, Aβ fibrils formed from Aβ$_{1-42}$ peptides with other known amyloid dyes, i.e., Thioflavin-T (ThT, at 200 μM) and 1-Fluoro-2,5-bis(3-carboxy-4-hydroxystyryl)benzene (FSB, at 200 μM) and examined by fluorescence microscopy (see, FIG. 10).

A representative compound of Formula I, i.e., Compound A, was administered intraperitoneally (i.p.) into 1 year old PS-APP mice (see, Borchelt et al., *Neuron*. (1997) 19:939-945, which is incorporated herein by reference) to assess the ability of compounds of the invention to pass through the blood brain barrier (BBB) and bind to Aβ peptide aggregate deposits (e.g., plaques) in vivo. In more detail, Compound A (10 μL or 1 μM solution per gram of body weight which is roughly equivalent to 5 mg/kg body weight) was injected into 1 year old PS-APP mice (n=2). One hour later, the mice were sacrificed and frozen sections of the frontal cortex were directly observed under a fluorescence microscope. Representative photomicrographs are shown in FIG. 11A. As shown in FIG. 11A, Aβ peptide aggregate deposits were stained by i.p. injected Compound A. The inset is the magnified image from a selected cortical area, showing the morphology of stained Aβ peptide aggregate deposits. The yellow dots were the result of autofluorescence. For visual clarity, the counterstain with nuclear dye was not shown. To confirm that the Compound A stained structures (see, FIG. 11B; left panel) was actually Aβ pepeptide aggregate deposits, the next contiguous sliced section was stained with the amyloid dye FSB (see, FIG. 11B; right panel), which has a different fluorescence emission spectrum than compound A. As indicated by the arrow in FIG. 11B, the objects stained by FSB correspond to those stained in vivo by Compound A. As a control, the frontal sections of a non-injected PS-APP mouse showed no Aβ peptide aggregate plaques staining (see, FIG. 11C; left panel), although the Aβ peptide aggregate plaques were present, which were subsequently demonstrated by staining the contiguous section with FSB (see, FIG. 11C; right panel). The sections shown were counterstained with a red nuclear dye.

The experimental results presented in FIG. 11A, FIG. 11B and FIG. 11C show that Compound A accumulated specifically in Aβ peptide aggregate plaques within 1 hour, with low background in both cortex and white matter. The bolus i.p. dosage used for this experiment was about half the amount of compound used for the i.p. injection of Pittsburgh Compound-B (PIB), an established amyloid ligand for clinical imaging (see, Bacskai et al. *Proc Natl Acad Sci USA* (2003) 100:12462-12467). Comparable to PIB, the fluorescence staining of Compound A remained at 3 hour and 24 hour after i.p. injection. In addition no apparent toxicity to mice (clinically and pathologically) was observed during the 24 hour period after injection.

Interestingly, and not unexpectedly in this experiment, the inventors did not observe any fluorescent staining of objects that was determined to be Aβ oligomers rather than fibrils. In particular, staining patterns reminiscent of the perineuronal synaptic-type deposit of AbO reported by Lacor et al. (*J. Neurosci*. (2004) 24:10191-10200) were not seen. Notably, 1 year old PS-APP mice do not have substantial amount of AβO; and as AβO are small and diffuse, their visualization in tissue requires high local concentrations or probes with affinities that are at least comparable to those suitable for neurotransmitter receptor or transporter imaging agents, e.g., KD's of ≦1 nM.

F. Imaging

The in vivo experimental results demonstrate that compounds or labeled compounds of Formula I can rapidly pass the BBB, can be retained by Aβ peptide aggregate deposits with a high degree of specificity, and have little short term toxicity. In addition to its therapeutic potential, compounds or labeled compounds of Formula I can be useful as imaging probes for detecting the presence of Aβ peptide aggregate deposits (e.g., plaques) in vivo (i.e., in a patient). As used herein, the term "imaging" refers to any method which permits the detection of a compound or labeled compound of Formula I.

1. In Vivo Imaging

Thus, in one aspect, the present invention provides for a method of detecting Aβ peptide aggregates in a patient comprising: i) administering to a patient a detectable quantity of a compound of Formula I, wherein the compound of Formula I binds to the Aβ peptide aggregates; and ii) imaging the patient to detect the presence of the compound of Formula I, thereby detecting the presence of Aβ peptide aggregates in the patient. In another aspect, the present invention provides for a method of detecting Aβ peptide aggregates in a patient comprising: i) administering to a patient a detectable quantity of a labeled compound of Formula I, wherein the labeled compound of Formula I binds to the Aβ peptide aggregates; and ii) imaging the patient to detect the presence of the labeled compound of Formula I, thereby detecting the presence of Aβ peptide aggregates in the patient. In certain embodiments, the method for detecting the presence of Aβ peptide aggregates utilized a radioactive compound of Formula I.

The method for detecting Aβ peptide aggregates in a patient preferably determines the presence and location of Aβ peptide aggregate deposits in an organ or body area, preferably brain, of a patient. In a one aspect of this embodiment, the patient is suspected of having a disease or condition selected from the group consisting of Lewy body diseases; cerebral amyloid angiopathy, Hereditary Cerebral Hemorrhage with Beta amyloidosis of the Dutch-Type, homozygotes for the apolipoprotein E4, inclusion body myosities and Niemann-Pick type C disease. In another embodiment, the patient is suspected from suffering from amyloidosis such as, for example, primary amyloidosis, secondary, amyloidosis, hereditary amyloidosis, hemodialysis associated amyloidosis, diabetes related amyloidosis, prion amyloidosis, Parkinson's related amyloidosis, amyloid neuropathy, among others.

In one embodiment, the step of detecting Aβ peptide aggregates in a patient by the disclosed methods is accomplished by gamma imaging, magnetic resonance imaging and magnetic resonance spectroscopy. In one aspect of this embodiment, the gamma imaging is either Positron Emission Tomography (PET) or Single Photon Emission Computed Tomography (SPECT). In one embodiment, the gamma imaging is done in conjunction with a CT (computed tomography) or MRI scan. For in vivo brain imaging purposes, the compounds and labeled compounds of Formula I are preferably administered to a patient by intravenous injection, and the ratio of (i) binding of a compound to a brain area other than the cerebellum to (ii) the binding of a compound to the cerebellum, in a patient suspected of having a disease or condition caused by Aβ peptide aggregation deposits is compared to the ratio determined in a "healthy" patient.

The invention employs Aβ peptide aggregate binding compounds or labeled compounds of Formula I as biomedical probes which, in conjunction with non-invasive neuroimaging techniques, such as, magnetic resonance spectroscopy (MRS) or imaging (MRI), or gamma imaging such as PET or SPECT, are used to quantify Aβ peptide aggregate deposition in vivo. For gamma imaging, the radiation emitted from the organ or area being examined is measured and expressed either as total binding or as a ratio in which total binding in one tissue is normalized to (for example, divided by) the total binding in another tissue of the same patient during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound. As used herein, a "patient" is a mammal, preferably a human, and most preferably a human suspected of having dementia.

For certain in vivo imaging purposes, the type of detection instrument available is a major factor in selecting a given label for a labeled compound. For instance, radioactive isotopes $^{11}$C and $^{19}$F are particularly suitable for in vivo imaging in the methods of the present invention. The type of instrument used will guide the selection of the radioisotope or stable isotope. For instance, the radioisotope chosen must have a type of decay detectable by a given type of instrument. Another consideration relates to the half-life of the radioisotope. The half-life should be long enough so that it is still detectable at the time of maximum uptake by the target, but short enough so that the host does not sustain deleterious radiation. The radioactive compounds of the invention can be detected using gamma imaging wherein emitted gamma irradiation of the appropriate wavelength is detected. Methods of gamma imaging include, but are not limited to, SPECT and PET. Preferably, for SPECT detection, the chosen radiolabel will lack a particulate emission, but will produce a large number of photons in a 140-200 keV range. For PET detection, the radiolabel will be a positron-emitting radionuclide such as .sup.19F which will annihilate to form two 511 keV gamma rays which will be detected by the PET camera.

Suitable radioisotopes for the imaging methods of the invention include beta-emitters, gamma-emitters, positron-emitters, and x-ray emitters. These radioisotopes include $^{131}$I, $^{124}$I, $^{18}$F, $^{11}$C, $^{13}$N, $^{15}$O, $^{75}$Br, and $^{76}$Br. The preferred radiolabels are $^{15}$O, $^{13}$N, $^{11}$C and $^{18}$F, or more preferably, $^{11}$C or $^{18}$F, for use in PET in vivo imaging; $^{123}$I for use in SPECT imaging; $^{19}$F for MRS/MRI; and $^{3}$H or $^{14}$C for in vitro studies. In addition, the imaging methods for detecting Aβ peptide aggregates in a patient may use compounds and labeled compounds of the invention having isotopes detectable by nuclear magnetic resonance spectroscopy. Stable isotopes particularly useful in magnetic resonance spectroscopy include $^{19}$F and $^{13}$C.

The imaging method disclosed above that utilize compound and labeled compounds of Formula I can be used to diagnose AD in mild or clinically confusing cases. This technique would also allow longitudinal studies of Aβ peptide aggregate deposition in human populations at high risk for Aβ peptide aggregate deposition such as Down's syndrome, familial AD, Hereditary Cerebral Hemorrhage with Beta amyloidosis of the Dutch-Type, and homozygotes for the apolipoprotein E4 allele. Corder et al., *Science* (1993) 261: 921. A method that allows the temporal sequence of Aβ peptide aggregate deposition to be followed can determine if deposition occurs long before dementia begins or if deposition is unrelated to dementia. This method can be used to monitor the effectiveness of therapies targeted at preventing Aβ peptide aggregate deposition.

Generally, in the imaging methods, the dosage of a compound of Formula I will vary depending on considerations such as age, condition, sex, and extent of disease in the patient, contraindications, if any, concomitant therapies and other variables, to be adjusted by a physician skilled in the art. Dosage can vary from 0.001 μg/kg to 10 μg/kg, preferably 0.01 μg/kg to 1.0 μg/kg.

Administration to the patient may be local or systemic and accomplished intravenously, intraarterially, intrathecally (via the spinal fluid) or the like. Administration may also be intradermal or intracavitary, depending upon the body site under examination. After a sufficient time has elapsed for the compound to bind with the Aβ peptide aggregate, for example 30 minutes to 48 hours, the area of the subject under investigation is examined by routine imaging techniques such as MRS/MRI, SPECT, planar scintillation imaging, PET and any emerging imaging techniques, as well. The exact protocol will necessarily vary depending upon factors specific to the patient, as noted above, and depending upon the body site under examination, method of administration and type of label used; the determination of specific procedures would be routine to the skilled artisan. For brain imaging, preferably, the amount (total or specific binding) of the bound radioactively labeled compound of Formula I is measured and compared (as a ratio) with the amount of labeled compound of Formula I bound to the cerebellum of the patient. This ratio is then compared to the same ratio in age-matched normal brain.

2. In Vitro Imaging

In another aspect, the present invention provides for in vitro imaging methods using compounds or labeled compounds of Formula I as imaging probes.

Accordingly, in one embodiment, the present invention relates to a method of detecting Aβ peptide aggregate deposits in biopsy or post-mortem tissue, the method comprises, (i) incubating a tissue suspected of having Aβ peptide aggregate deposits with a compound or labeled compound of Formula I; and (ii) imaging the tissue to detect Aβ peptide aggregates in the tissue. In one embodiment, the method of detecting Aβ peptide aggregate deposits in biopsy or post-mortem tissue involves incubating formalin-fixed tissue with a solution of an Aβ peptide aggregate binding compound or labeled compound of Formula I. Preferably, the solution is 25-100% ethanol, (with the remainder being water) saturated with a Aβ peptide aggregate binding compound or labeled compound according to the invention. Upon incubation, the compound stains or labels the Aβ peptide aggregate deposit in the tissue, and the stained or labeled deposit can be detected or visualized by any standard method. Such detection means include fluorescence imaging and microscopic techniques such as bright-field, laser-confocal and cross-polarization microscopy.

The method of quantifying the amount of Aβ peptide aggregates in biopsy or post-mortem tissue involves incubating a compound or labeled compound of Formula I with a homogenate of biopsy or post-mortem tissue. The tissue is obtained and homogenized by methods well known in the art. The preferred label is a radioisotope, although other labels such as enzymes, chemiluminescent and immunofluorescent compounds are well known to skilled artisans. In one embodiment, the radioisotope is $^{125}$I, $^{14}$C or $^{3}$H. Tissue containing Aβ peptide aggregate deposits will bind to the labeled compounds of the present invention. The bound tissue is then separated from the unbound tissue by any mechanism known to the skilled artisan, such as filtering. The bound tissue can then be quantified through any means known to the skilled artisan. The units of tissue-bound labeled compound of Formula I are then converted to units of micrograms of Aβ peptide aggregate per 100 mg of tissue by comparison to a standard curve generated by incubating known amounts of Aβ peptide aggregates with the labeled compound of Formula I.

Suitable radioisotopes for in vitro quantification of Aβ peptide aggregate in homogenates of biopsy or post-mortem tissue include $^{125}$I, $^{14}$C, and $^{3}$H.

What is claimed is:
1. A compound of Formula I:

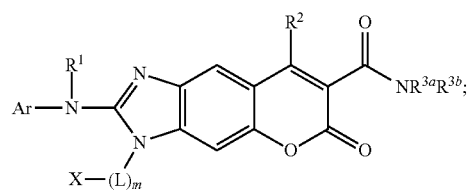

or a pharmaceutically acceptable salt thereof, wherein in Formula I:
L is $C_{1-6}$ alkylene;
X is phenyl substituted with fluorine, bromine or iodine;
Ar is phenyl substituted at the 4-position with one substituent selected from the group consisting of perfluoro($C_1$-$C_4$)alkoxy and —OR$^c$;
wherein R$^c$ is $C_{1-4}$ alkyl;
R$^1$ is a member selected from the group consisting of hydrogen, $C_{1-6}$ alkyl and $C_{1-6}$ haloalkyl;
R$^2$ is a member selected from the group consisting of hydrogen, halogen, $C_{1-6}$ alkoxy, $C_{1-6}$ alkylamino, $C_{1-6}$ dialkylamino, $C_{1-6}$ alkyl and $C_{1-6}$ haloalkyl;
R$^{3a}$ and R$^{3b}$ are each a member independently selected from the group consisting of hydrogen, $C_{1-6}$ alkyl, $C_{1-6}$ haloalkyl, and $C_{1-6}$ alkoxy, and wherein R$^{3a}$ and R$^{3b}$ and the nitrogen atom to which each is attached are optionally combined to form a 5- to 6-membered ring; and
the subscript m is 1.

2. The compound of claim 1, wherein L is selected from the group consisting of —CH$_2$—, —CH$_2$CH$_2$—, —CH$_2$CH$_2$CH$_2$—, and —CH$_2$CH$_2$CH$_2$CH$_2$—.

3. The compound of claim 1, wherein L is selected from the group consisting of —CH$_2$—, —CH$_2$CH$_2$—, and —CH$_2$CH$_2$CH$_2$—.

4. The compound of claim 1, wherein Ar is selected from the group consisting of:

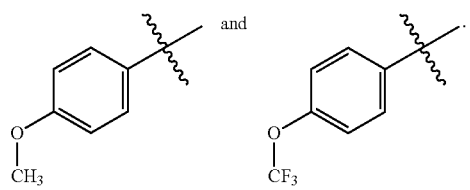

5. The compound of claim 1, wherein said compound is of Formula Ia

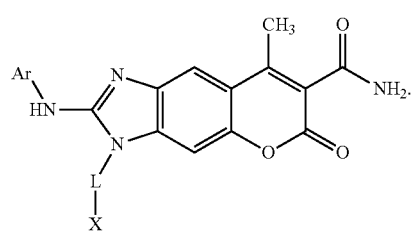

6. The compound of claim 1, wherein said compound is selected from the group consisting of
- 3-(3-iodo-benzyl)-2-(4-methoxy-phenylamino)-8-methyl-6-oxo-3,6-dihydrochromeno [6,7-d]imidazole-7-carboxylic acid amide;
- 3-(3-bromobenzyl)-2-(4-methoxyphenylamino)-8-methyl-6-oxo-3,6-dihydrochromeno [7,6-d]imidazole-7-carboxylic acid amide;
- 3-(3-fluorobenzyl)-2-(4-methoxyphenylamino)-8-methyl-6-oxo-3,6-dihydrochromeno [7,6-d]imidazole-7-carboxylic acid amide;
- 3-(4-bromobenzyl)-2-(4-methoxyphenylamino)-8-methyl-6-oxo-3,6-dihydrochromeno [7,6-d]imidazole-7-carboxylic acid amide;
- 3-(4-iodobenzyl)-2-(4-methoxyphenylamino)-8-methyl-6-oxo-3,6-dihydrochromeno [7,6-d]imidazole-7-carboxylic acid amide;
- 3-(4-bromophenethyl)-2-(4-methoxyphenylamino)-8-methyl-6-oxo-3,6-dihydrochromeno [7,6-d]imidazole-7-carboxylic acid amide;
- 3-(3-bromobenzyl)-8-methyl-6-oxo-2-(4-(trifluoromethoxy)phenylamino)-3,6-dihydrochromeno [7,6-d]imidazole-7-carboxylic acid amide;
- 3-(3-iodobenzyl)-8-methyl-6-oxo-2-(4-(trifluoromethoxy)phenylamino)-3,6-dihydrochromeno [7,6-d]imidazole-7-carboxylic acid amide; and
- 3-(4-bromobenzyl)-8-methyl-6-oxo-2-(4-(trifluoromethoxy)phenylamino)-3,6-dihydrochromeno [7,6-d]imidazole-7-carboxylic acid amide.

7. The compound of claim 1, wherein said compound is selected from the group consisting of:

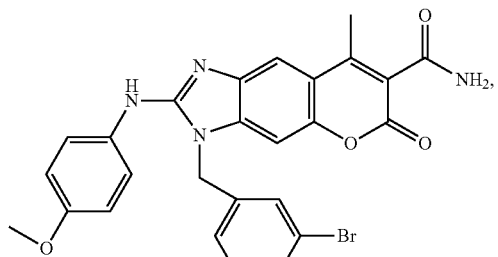

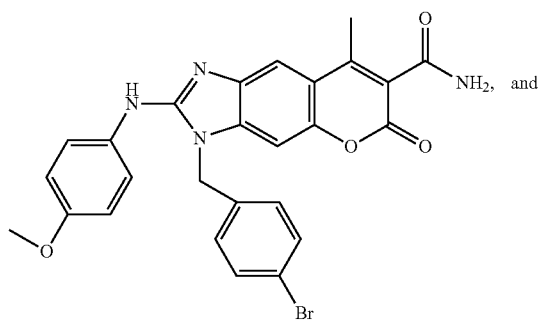

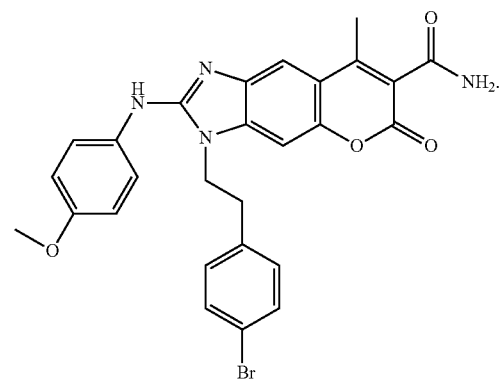

8. The compound of claim 1, wherein said compound is:

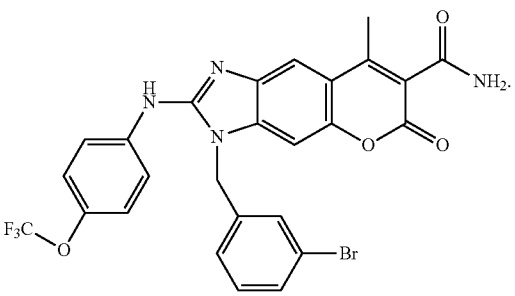

9. The compound of claim 1, wherein said compound is selected from the group consisting of:

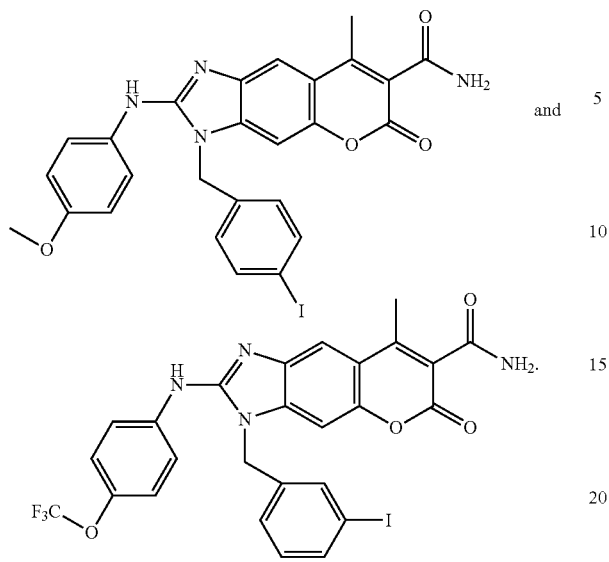 and
10. The compound of claim 1, wherein said compound is:
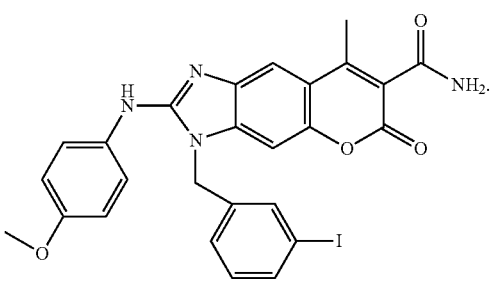
* * * * *